(12) United States Patent
Gotoh et al.

(10) Patent No.: US 6,791,681 B2
(45) Date of Patent: Sep. 14, 2004

(54) APPARATUS AND METHOD FOR DETERMINING EXISTENCE RANGE OF FOREIGN SUBSTANCE

(75) Inventors: Yasuhiro Gotoh, Kadoma (JP); Seiji Nishiwaki, Kobe (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 83 days.

(21) Appl. No.: 10/172,084

(22) Filed: Jun. 13, 2002

(65) Prior Publication Data

US 2002/0190702 A1 Dec. 19, 2002

(30) Foreign Application Priority Data

Jun. 14, 2001 (JP) ............................... 2001-179709
Jul. 24, 2001 (JP) ............................... 2001-222889

(51) Int. Cl.[7] ............................................. G01N 21/00
(52) U.S. Cl. ............................ 356/237.3; 356/237.1; 250/559.28
(58) Field of Search ...................... 356/237.1–237.6; 250/559.28, 559.31; 369/44.25, 44.28, 53.23, 53.31, 112

(56) References Cited

U.S. PATENT DOCUMENTS

| | | | | |
|---|---|---|---|---|
| 3,844,659 A | * | 10/1974 | Baganoff | ................. 356/32 |
| 4,340,950 A | * | 7/1982 | Kosaka | ................. 369/44.25 |
| 4,730,290 A | * | 3/1988 | Takasago et al. | ......... 369/30.21 |
| 4,789,978 A | * | 12/1988 | Shikama et al. | ....... 369/112.23 |
| 5,184,343 A | * | 2/1993 | Johann et al. | ........... 369/53.15 |
| 5,210,731 A | * | 5/1993 | Katumata | ................. 369/44.28 |
| 5,668,786 A | * | 9/1997 | Sasaki et al. | ............ 369/13.32 |
| 5,963,523 A | * | 10/1999 | Kayama et al. | .......... 369/53.22 |
| 6,201,780 B1 | * | 3/2001 | Katayama | .............. 369/112.19 |
| 6,400,662 B1 | * | 6/2002 | Choi et al. | ............... 369/44.28 |

FOREIGN PATENT DOCUMENTS

JP          06-223384          8/1994

* cited by examiner

*Primary Examiner*—Frank G. Font
*Assistant Examiner*—Sang H. Nguyen
(74) *Attorney, Agent, or Firm*—Snell & Wilmer, LLP

(57) ABSTRACT

An apparatus for determining an existence range of a foreign substance which is present on a surface of an object, includes: an optical system including a light source for emitting a light beam on to the surface of the object; a movement section for relatively moving the object with respect to the light beam; a light detection section for detecting a light quantity of the light beam reflected by the surface of the object to generate a light detection signal which indicates the light quantity; a difference signal generation section for generating a difference signal; a perimeter signal generation section for comparing the difference signal with a reference value to generate a perimeter signal; and a foreign substance determination section for determining an existence range of the foreign substance using the perimeter signal.

36 Claims, 13 Drawing Sheets center line centroid of amplitude center line

FIG. 9
(a)
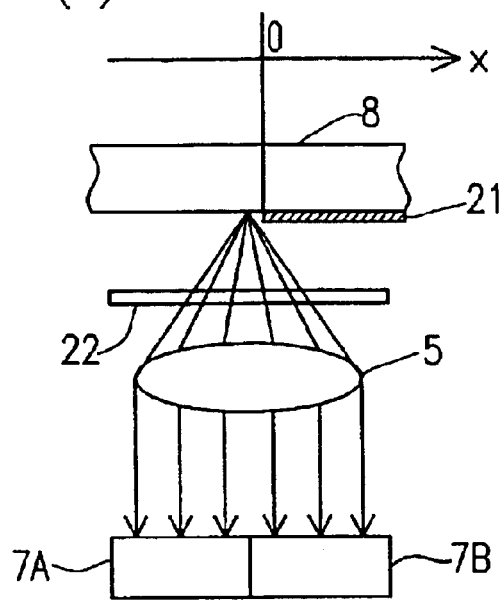
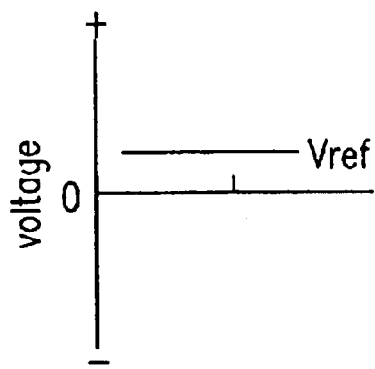
(b)
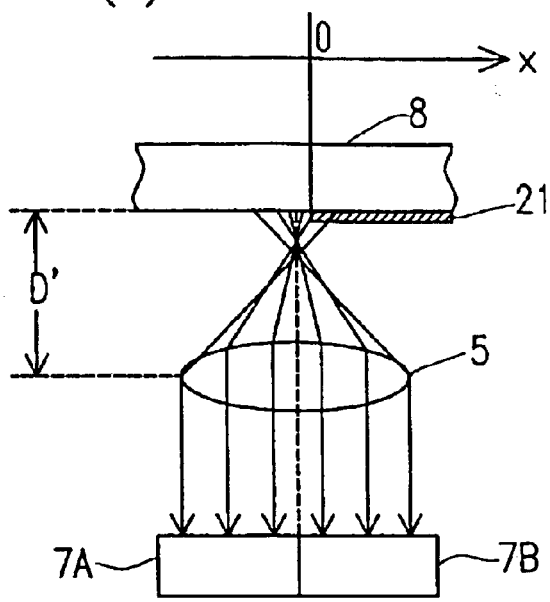
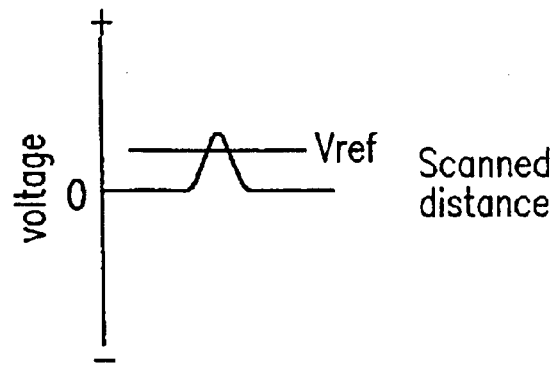

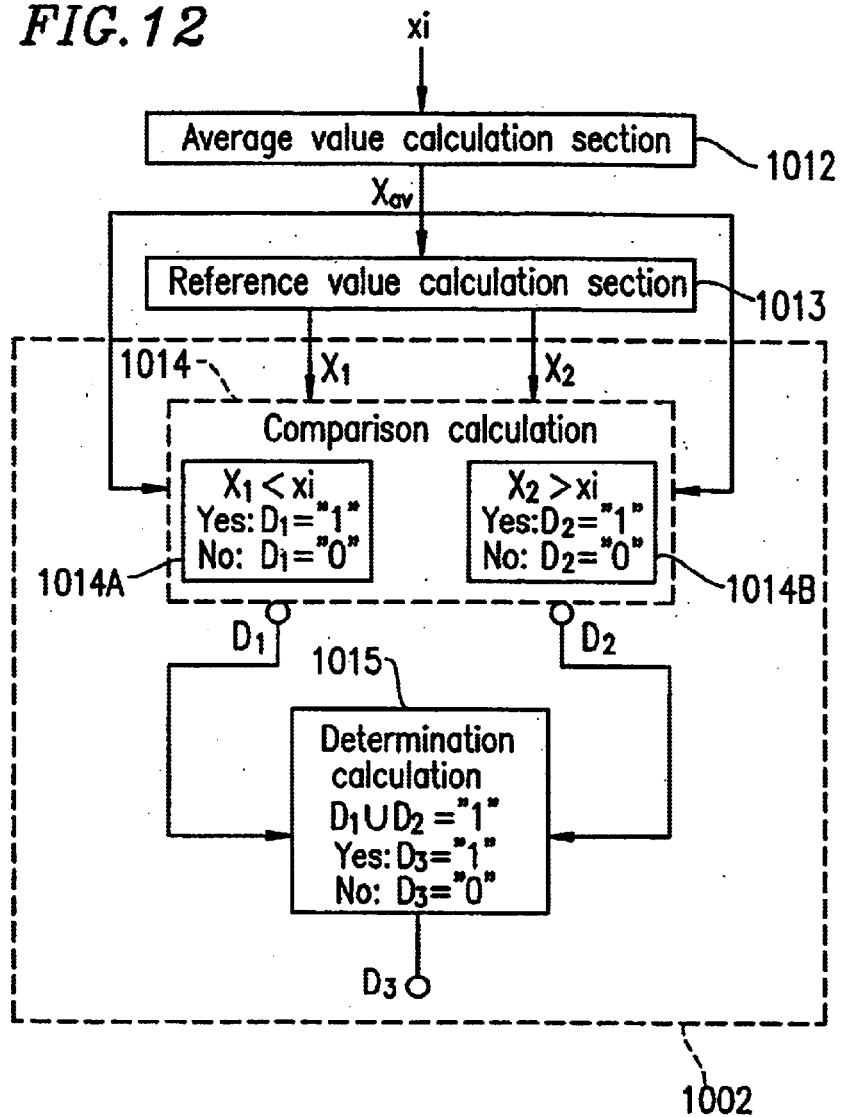

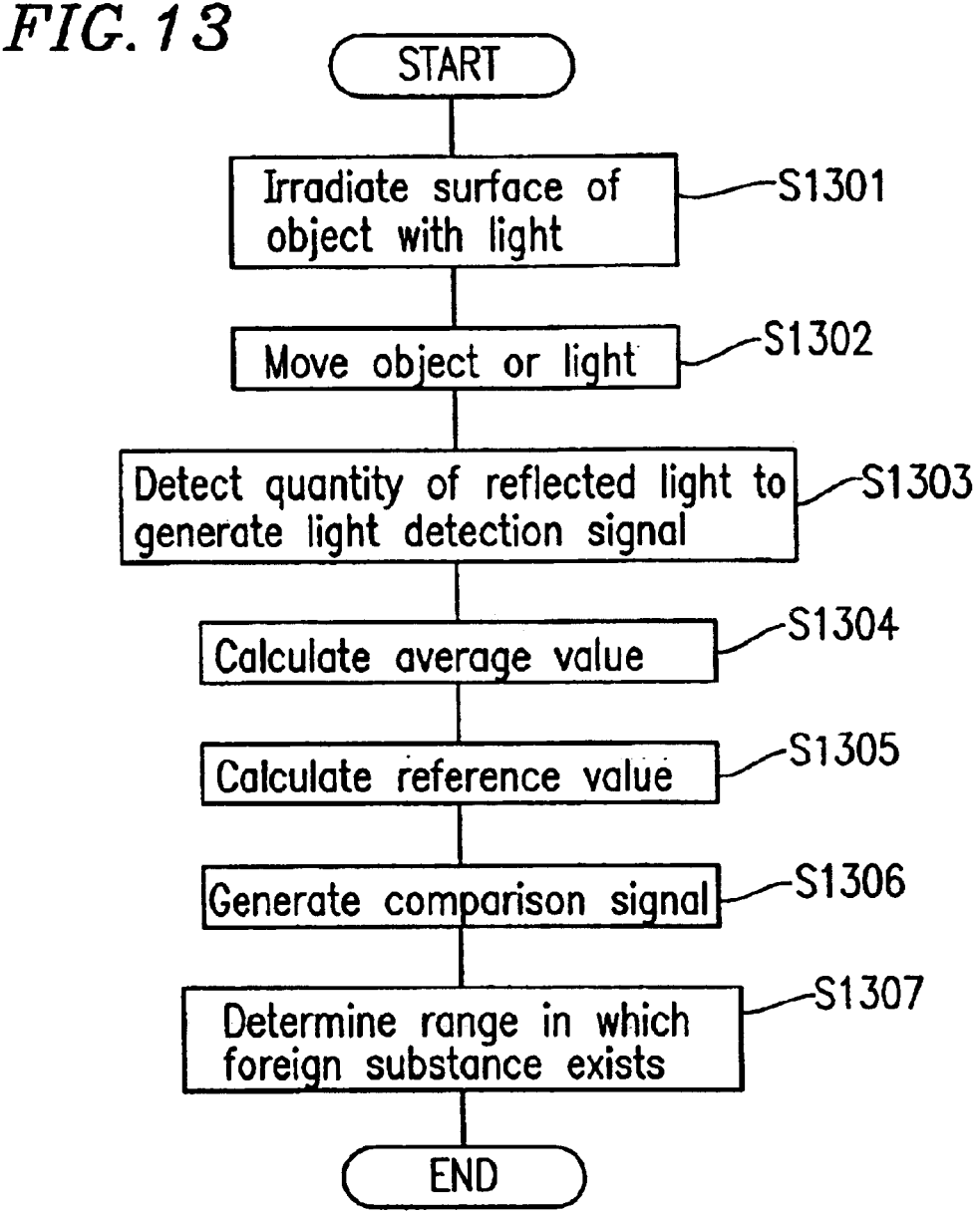

APPARATUS AND METHOD FOR DETERMINING EXISTENCE RANGE OF FOREIGN SUBSTANCE

BACKGROUND OF THE INVENTION

1. Field of the Invention

The present invention relates to an apparatus and method for optically determining a range in which a foreign substance attached to a surface of an object, such as dirt, dust, an oil film, a fingerprint, a scratch, flaws, or the like, exists.

2. Description of the Related Art

In recent years, in the field of recording mediums, such as optical discs, magnetic discs, magnetic tapes, etc., in the field of color filters for a liquid crystal display and organic EL display, and in the field of electronic devices, such as semiconductor integrated circuit, or the like, the size of a component incorporated in a product has been reduced to a very small size. As already known in the above fields, along with a significant reduction in the component size, a foreign substance, such as dirt, dust, scratches, etc., attached to an electronic device, which did not cause a significant problem before, brings about a greater adverse influence on the production yield and performance during operation of the electronic device. Thus, an apparatus and method for detecting a foreign substance with high accuracy has heightened in demand. Conventionally, various proposals have been made for such an apparatus and method. One known example of such is a foreign substance detection apparatus disclosed in Japanese Laid-Open Publication No. 6-223384.

FIG. 15 shows a structure of a conventional foreign substance detection apparatus 1500 for use with an optical disc. The foreign substance detection apparatus 1500 includes: a light source 91; an objective lens 92; a quarter waveplate 94; a polarized beam splitter 95; a light receiving element 96; an I-V conversion section 97; and a sum signal generation circuit 98. The light source 91 is, for example, a semiconductor laser. The light receiving element 96 is separated into a first light receiving element 96A and a second light receiving element 96B. The I-V conversion section 97 includes a first I-V conversion circuit 97A and a second I-V conversion circuit 97B.

Next, an operation of the foreign substance detection apparatus 1500 for detecting a foreign substance which is present on an optical disc 93 is described.

The light source 91 emits a light beam toward the optical disc 93. The emitted light beam passes through the polarized beam splitter 95 and the quarter waveplate 94. Then, the light beam is converged by the objective lens 92 on the surface of the optical disc 93 so as to form a light spot thereon. The light beam reflected by the surface of the optical disc 93 passes through the objective lens 92 and the quarter waveplate 94 again, whereby the phase of the light beam is changed. The light beam with the changed phase is reflected by the polarized beam splitter 95 so as to enter the first light receiving element 96A and the second light receiving element 96B. The first light receiving element 96A and the second light receiving element 96B respectively generate a first electric current signal $I_A$ and a second electric current signal $I_B$, each of which indicates the quantity of the received light beam. The first electric current signal $I_A$ and the second electric current signal $I_B$ are transmitted to the first I-V conversion circuit 97A and the second I-V conversion circuit 97B, respectively.

The first I-V conversion circuit 97A and the second I-V conversion circuit 97B convert the respective first electric current signal $I_A$ and the second electric current signal $I_B$ into a first voltage signal $V_A$ and a second voltage signal $V_B$, respectively. The first voltage signal $V_A$ and the second voltage signal $V_B$ are transmitted to the sum signal generation circuit 98.

The sum signal generation circuit 98 sums up the first voltage signal $V_A$ and the second voltage signal $V_B$ to generate a sum voltage signal $V_A+V_B$. The sum signal generation circuit 98 compares the generated sum voltage signal $V_A+V_B$ with a reference voltage signal $V_{ref}$. The reference voltage signal $V_{ref}$ is a voltage signal which indicates the quantity of light calculated from the theoretical reflectance of the optical disc 93 on which no foreign substance is attached.

If the relationship between the reference voltage signal $V_{ref}$ and the sum voltage signal $V_A+V_B$ is $V_{ref}<V_A+V_B$ or $V_{ref}>V_A+V_B$, the foreign substance detection apparatus 1500 determines that there is a foreign substance present. If the relationship between the reference voltage signal $V_{ref}$ and the sum voltage signal $V_A+V_B$ is $V_{ref}=V_A+V_B$, the foreign substance detection apparatus 1500 determines that there is no foreign substance present.

The foreign substance detection apparatus 1500 has two light receiving elements (the first light receiving element 96A and the second light receiving element 96B), but may have a single light receiving element.

The above described foreign substance detection apparatus 1500 mainly has the two problems (1) and (2) described below.

(1) In the case where the difference between the reflectance of an object (object to be examined) and that of a foreign substance is small, the foreign substance on the object sometimes cannot be accurately detected. Such applies especially to the case of a foreign substance, such as an oil film, a fingerprint, or the like. In this case, a large difference does not occur between the quantity of light reflected by a portion of the object on which the foreign substance exists and the quantity of light reflected by a portion of the object on which the foreign substance does not exist (i.e., a large difference does not occur between the sum voltage signal obtained from the quantity of light reflected by a portion of the object on which the foreign substance exists and the reference voltage signal obtained from the quantity of light reflected by a portion of the object on which the foreign substance does not exist). Accordingly, it is impossible to accurately detect the foreign substance.

Thus, in order to accurately detect such a foreign substance, it is necessary to stabilize the sum voltage signal with high accuracy. However, under a normal environment for using such a detection apparatus, the quantity of light readily varies due to a variation with time, and a variation due to temperature of a light source, a light receiving element, a signal processing circuit, or the like, or due to dust attached to an optical lens, a light receiving element, or the like. Thus, it is difficult to stabilize the sum voltage signal which is generated in a subsequent component. From experimentation conducted by the present inventors, it was confirmed that the sum voltage signal can vary by about 50% under a normal environment.

The sum voltage signal can be stabilized to some extent by using the foreign substance detection apparatus in a clean room, by incorporating a high-precision, complicated control apparatus, by periodically performing maintenance activities, or the like. However, in such cases, the cost efficiency is decreased.

(2) In the conventional foreign substance detection apparatus 1500, the reference voltage signal $V_{ref}$ used for determining the presence/absence of a foreign substance is a fixed voltage signal which indicates, for example, the quantity of light calculated from the theoretical reflectance of an object on which no foreign substance is attached. However, as described above, under an actual environment for using the detection apparatus, the quantity of light reflected by the surface of the object readily varies. Accordingly, the quantity of light reflected by a portion of the object on which no foreign substance is attached, which is measured under the normal environment, is sometimes different from the quantity of light calculated from the theoretical reflectance of the object. As a result, accuracy in detection of a foreign substance decreases.

SUMMARY OF THE INVENTION

According to one aspect of the present invention, an apparatus for determining an existence range of a foreign substance which is present on a surface of an object, includes: an optical system including a light source for emitting a light beam onto the surface of the object; a movement section for relatively moving the object with respect to the light beam; a light detection section for detecting a light quantity of the light beam reflected by the surface of the object to generate a light detection signal which indicates the light quantity, the light detection section including a first light detection section for generating a first light detection signal and a second light detection section for generating a second light detection signal; a difference signal generation section for generating a difference signal which indicates a difference between the first light detection signal and the second light detection signal; a perimeter signal generation section for comparing the difference signal with a reference value to generate a perimeter signal which indicates a perimeter of the foreign substance; and a foreign substance determination section for determining an existence range of the foreign substance using the perimeter signal.

In one embodiment of the present invention, the first light detection section and the second light detection section are arranged along the moving direction in this order.

In another embodiment of the present invention, the reference value varies according to an average value of the light quantity of the light beam reflected by the surface of the object on which the foreign substance is not attached.

In still another embodiment of the present invention, the optical system further includes a converging section for converging the light beam on the surface of the object; and the converging section is arranged such that the converged light beam has a wavefront aberration.

In still another embodiment of the present invention, the light beam is monochromic light; and a standard deviation of the wavefront aberration is 0.07 or more times a wavelength of the monochromic light.

In still another embodiment of the present invention, the apparatus further includes a vibration section for vibrating the converging section along a direction parallel to the surface of the object.

In still another embodiment of the present invention, the movement section reciprocates the light beam along a direction parallel to the surface of the object.

In still another embodiment of the present invention, the apparatus further includes a rotation section for rotating the object.

In still another embodiment of the present invention, the movement section oscillates the light beam in a direction perpendicular to the rotation direction of the object.

In still another embodiment of the present invention, the movement section reciprocates the object along a direction perpendicular to the emission direction of the light beam.

According to another aspect of the present invention, a method for determining an existence range of a foreign substance which is present on a surface of an object, includes steps of: emitting a light beam onto the surface of the object; relatively moving the object with respect to the light beam; detecting a light quantity of the light beam reflected by the surface of the object using a light detection section, to generate a light detection signal which indicates the light quantity, the light detection section including a first light detection section for generating a first light detection signal and a second light detection section for generating a second light detection signal; generating a difference signal which indicates a difference between the first light detection signal and the second light detection signal; comparing the difference signal with a reference value to generate a perimeter signal which indicates a perimeter of the foreign substance; and determining an existence range of the foreign substance using the perimeter signal.

In one embodiment of the present invention, the first light detection section and the second light detection section are arranged along the moving direction in this order.

In another embodiment of the present invention, the reference value varies according to an average value of the light quantity of the light beam reflected by the surface of the object on which the foreign substance is not attached.

In still another embodiment of the present invention, the method further includes a step of converging the light beam on the surface of the object, wherein the light beam converged on the surface of the object has a wavefront aberration.

In still another embodiment of the present invention, the light beam is monochromic light; and a standard deviation of the wavefront aberration is 0.07 or more times a wavelength of the monochromic light.

In still another embodiment of the present invention, the step of converging the light beam includes a step of vibrating the light beam over the surface of the object.

In still another embodiment of the present invention, the moving step includes a step of reciprocating the light beam along a direction parallel to the surface of the object.

In still another embodiment of the present invention, the moving step includes a step of rotating the object.

In still another embodiment of the present invention, the moving step includes a step of oscillating the light beam in a direction perpendicular to the rotation direction of the object.

In still another embodiment of the present invention, the moving step includes a step of reciprocating the object along a direction perpendicular to the emission direction of the light beam.

According to still another aspect of the present invention, an apparatus for determining an existence range of a foreign substance which is present on a surface of an object, includes: an optical system including a light source for emitting a light beam onto the surface of the object: a movement section for relatively moving the object with respect to the light beam; a light detection section for detecting a light quantity of the light beam reflected by the surface of the object to generate a light detection signal which indicates the light quantity; an average value calculation section for calculating an average value of the light detection signal; a reference value calculation section for calculating a reference value using a function where the average value is a variable; a comparison signal generation section for comparing the light detection signal with the reference value to generate a comparison signal which indicates presence/absence of the foreign substance; and a foreign substance determination section for determining an existence range of the foreign substance using the comparison signal.

In one embodiment of the present invention, the average value is calculated by the average value calculation section by: obtaining an average value by averaging all values of the light detection signal which indicates the light quantity of the light beam reflected from the surface of the object on which the foreign substance is not attached; and averaging the values of the light detection signal which do not exceed a standard deviation of the obtained average value.

In another embodiment of the present invention, the reference value includes a first reference value $X_1$ and a second reference value $X_2$; the first reference value $X_1$ is used for detecting a foreign substance whose reflectance $n_{var}$ is larger than a reflectance $n_{ob}$ of the object ($n_{ob} < n_{var}$); and the second reference value $X_2$ is used for detecting a foreign substance whose reflectance $n_{var}$ is smaller than the reflectance $n_{ob}$ of the object ($n_{ob} > n_{var}$).

In still another embodiment of the present invention, the first reference value $X_1$ and the second reference value $X_2$ are calculated based on an arithmetic operation formula selected from a group consisting of following arithmetic operation formulas:

$$X_1 = X_{av} \cdot (1+\beta_1), X_2 = X_{av} \cdot (1-\alpha_1);$$

$$X_1 = X_{av}/(1-\alpha_2), X_2 = X_{av}/(1+\beta_2); \text{ and}$$

$$X_1 = X_{av} + \beta_3, X_2 = X_{av} - \alpha_3,$$

where $X_{av}$ denotes the average value; $\alpha_1, \alpha_2, \alpha_3, \beta_1, \beta_2, \beta_3 > 0$; and $\alpha_1, \alpha_2, \alpha_3, \beta_1, \beta_2, \beta_3$ are constants.

In still another embodiment of the present invention, the movement section reciprocates the light beam along a direction parallel to the surface of the object.

In still another embodiment of the present invention, the apparatus further includes a rotation section for rotating the object.

In still another embodiment of the present invention, the movement section oscillates the light beam in a direction perpendicular to the rotation direction of the object.

In still another embodiment of the present invention, the movement section reciprocates the object along a direction perpendicular to the emission direction of the light beam.

According to still another aspect of the present invention, a method for determining an existence range of a foreign substance which is present on a surface of an object, includes steps of: emitting a light beam onto the surface of the object; relatively moving the object with respect to the light beam; detecting a light quantity of the light beam reflected by the surface of the object to generate a light detection signal which indicates the light quantity; calculating an average value of the light detection signal; calculating a reference value using a function where the average value is a variable; comparing the light detection signal with the reference value to generate a comparison signal which indicates presence/absence of the foreign substance; and determining an existence range of the foreign substance using the comparison signal.

In one embodiment of the present invention, the step of calculating the average value includes: obtaining an average value by averaging all values of the light detection signal which indicates the light quantity of the light beam reflected from the surface of the object on which the foreign substance is not attached; and averaging the values of the light detection signal which do not exceed a standard deviation of the obtained average value.

In another embodiment of the present invention, the reference value includes a first reference value $X_1$ and a second reference value $X_2$; the first reference value $X_1$ is used for detecting a foreign substance whose reflectance $n_{var}$ is larger than a reflectance $n_{ob}$ of the object ($n_{ob} < n_{var}$); and the second reference value $X_2$ is used for detecting a foreign substance whose reflectance $n_{var}$ is smaller than the reflectance $n_{ob}$ of the object ($n_{ob} > n_{var}$).

In still another embodiment of the present invention, the step of calculating the reference value includes a step of obtaining the first reference value $X_1$ and the second reference value $X_2$ based on an arithmetic operation formula selected from a group consisting of following arithmetic operation formulas:

$$X_1 = X_{av} \cdot (1+\beta_1), X_2 = X_{av} \cdot (1-\alpha_1);$$

$$X_1 = X_{av}/(1-\alpha_2), X_2 = X_{av}/(1+\beta_2); \text{ and}$$

$$X_1 = X_{av} + \beta_3, X_2 = X_{av} - \alpha_3,$$

where $X_{av}$ denotes the average value; $\alpha_1, \alpha_2, \alpha_3, \beta_1, \beta_2, \beta_3 > 0$; and $\alpha_1, \alpha_2, \alpha_3, \beta_1, \beta_2, \beta_3$ are constants.

In still another embodiment of the present invention, the moving step includes a step of reciprocating the light beam along a direction parallel to the surface of the object.

In still another embodiment of the present invention, the moving step includes a step of rotating the object.

In still another embodiment of the present invention, the moving step includes a step of oscillating the light beam in a direction perpendicular to the rotation direction of the object.

In still another embodiment of the present invention, the moving step includes a step of reciprocating the object along a direction perpendicular to the emission direction of the light beam.

Thus, the invention described herein makes possible the advantages of (i) providing an apparatus and method capable of detecting, with high accuracy, a foreign substance on an object in the case where a difference between the reflectance of the object and that of the foreign substance is small; and (ii) providing an apparatus and method capable of detecting a foreign substance with high accuracy, and capable of detecting the range on an object in which a foreign substance exists regardless of a variation in the quantity of light reflected by the object which is caused according to the environment for using the apparatus.

These and other advantages of the present invention will become apparent to those skilled in the art upon reading and understanding the following detailed description with reference to the accompanying figures.

BRIEF DESCRIPTION OF THE DRAWINGS

FIG. 9 shows a difference voltage signal generated from a light beam having a wavefront aberration, and a difference voltage signal generated from a light beam not having a wavefront aberration, in the foreign substance existence range determination apparatus 100 according to embodiment 1 of the present invention.

FIG. 12 illustrates an arithmetic process in a determination section 1002 of the foreign substance existence range determination apparatus 1000.

FIG. 13 is a flowchart which illustrates a method for determining an existence range of a foreign substance using the foreign substance existence range determination apparatus 1000 according to embodiment 2 of the present invention.

DESCRIPTION OF THE PREFERRED EMBODIMENTS

Hereinafter, embodiments of the present invention will be described with reference to the drawings.

Embodiment 1

Figure 1:
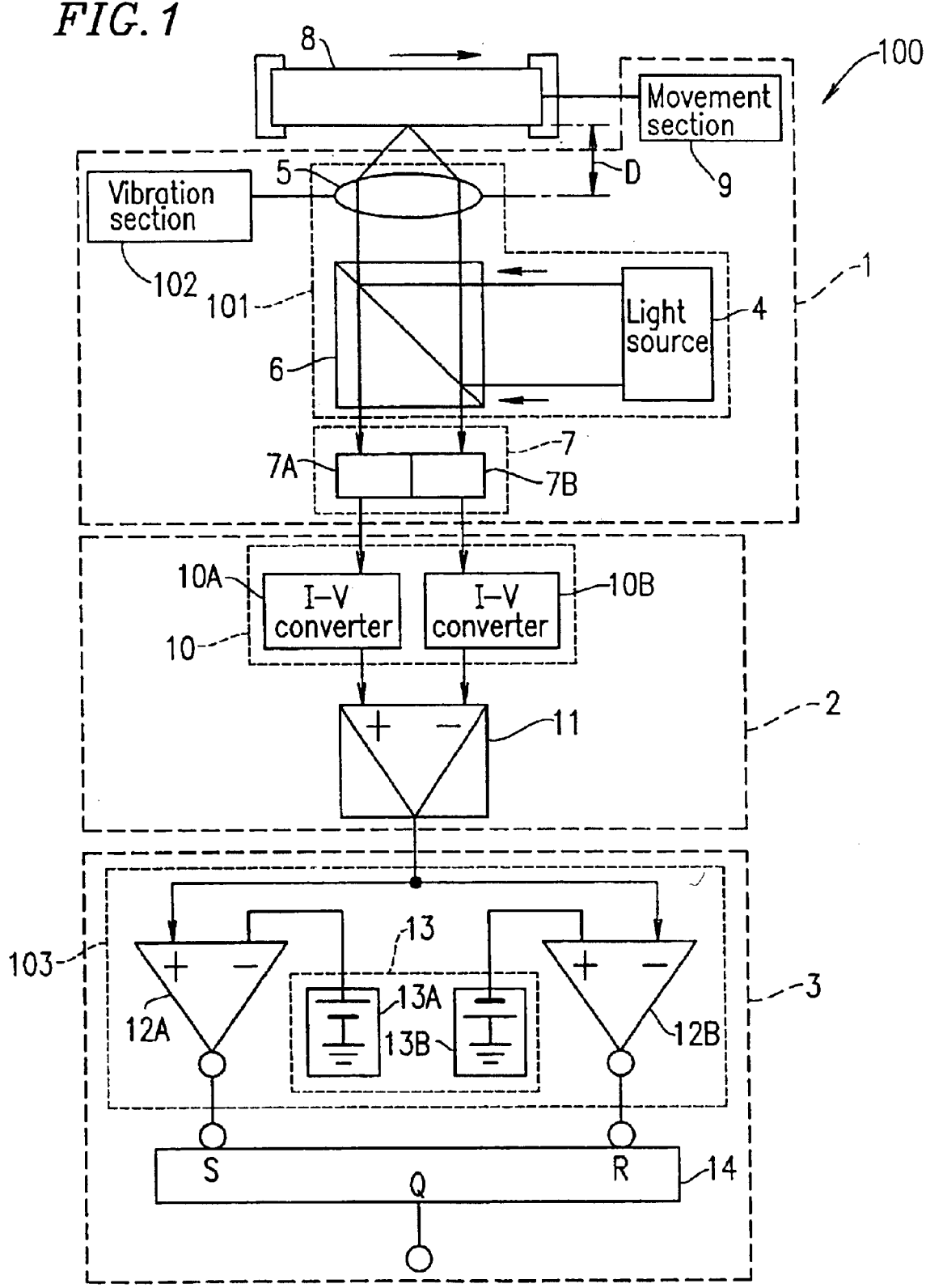
FIG. 1 shows a structure of a foreign substance existence range determination apparatus 100 according to embodiment 1 of the present invention.

FIG. 1 shows a structure of a foreign substance existence range determination apparatus 100 according to embodiment 1 of the present invention. The foreign substance existence range determination apparatus 100 optically determines a range on a surface of an object 8 in which a foreign substance exists. The foreign substance existence range determination apparatus 100 includes a light detection section 1, a signal generation section 2, and a determination section 3. The object 8 may be, for example, an optical disc, a magnetic disc, etc.

The light detection section 1 irradiates the surface of the object 8 with a light beam, detects the quantity of light reflected by the surface of the object 8, and generates an electric signal which indicates the quantity of reflected light. The light detection section 1 includes an optical system 101, a light detection portion 7, a movement section 9, and a vibration section 102. The optical system 101 includes a light source 4, a converging section 5, and a beam splitter 6.

The light source 4 may be, for example, an incandescent lamp, a halogen lamp, a semiconductor laser, a gas laser, etc. The light source 4 may preferably be a laser light source, such as a semiconductor laser, a gas laser, or the like. Since a laser light source is a source of coherent light, a foreign substance on the surface of an object can be detected with high accuracy.

The converging section 5 may be, for example, an objective lens. The converging section 5 converges the light beam, which was emitted by the light source 4 and reflected by the beam splitter 6, onto the surface of the object 8 so as to form a light spot thereon.

The diameter and shape of the light spot formed on the object 8 are changed by appropriately selecting an optical system according to the type of the object, the type and size of a foreign substance to be detected, etc. The diameter of the light spot is suitably in the range of 1 $\mu$m to 5 $\mu$m, but the present invention is not limited to this range. The diameter of the light spot can be changed by any method, for example, by moving a focal point of the converging section 5, by using an optical system which can generate a desired spot diameter, etc.

The shape of the light spot may be any shape, such as a circular shape, an oval shape, a rectangular shape, etc., which is determined according to the type and size of the object and a foreign substance to be detected. The shape of the light spot can be changed by any method, for example, by inserting a mask having a desired shape in the optical path, by using a cylindrical lens, etc.

The movement section 9 may be any movement means capable of moving the object 8 with respect to the light beam from the light source 4. Alternatively, the movement section 9 may be structured so as to move the light beam from the light source 4 with respect to the object 8.

The vibration section 102 is connected to the converging section 5, and vibrates the converging section 5. The vibration section 102 may be, for example, an electromagnetic actuator. By vibrating the converging section 5 with the vibration section 102, the trail of the light beam on the surface of the object 8 vibrates.

Figure 2:
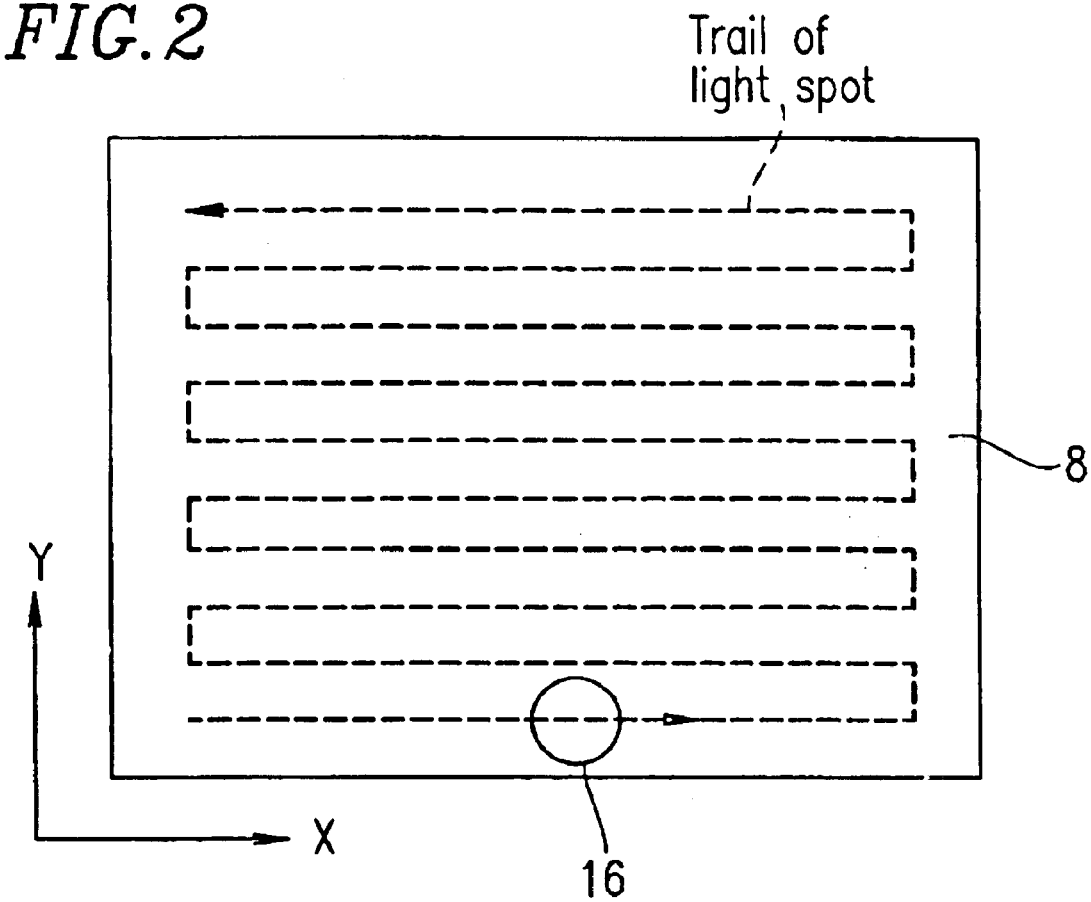
FIG. 2 shows a trail of a light spot 16 on a surface of an object 8.

FIG. 2 shows a trail of a light spot 16 on the surface of the object 8. In the case where the object 8 has a rectangular shape, it is desirable that the movement section 9 reciprocates the object 8 along the x-direction and y-direction, such that the light spot 16 moves as shown by the broken line in FIG. 2. In the case where the light source 4 is a laser light source, the movement section 9 moves the object 8 along only the y-direction, while the light beam from the light source 4 is moved along the x-direction by using a polygon mirror (not shown), whereby the light spot 16 moves as shown by the broken line in FIG. 2.

Figure 3:
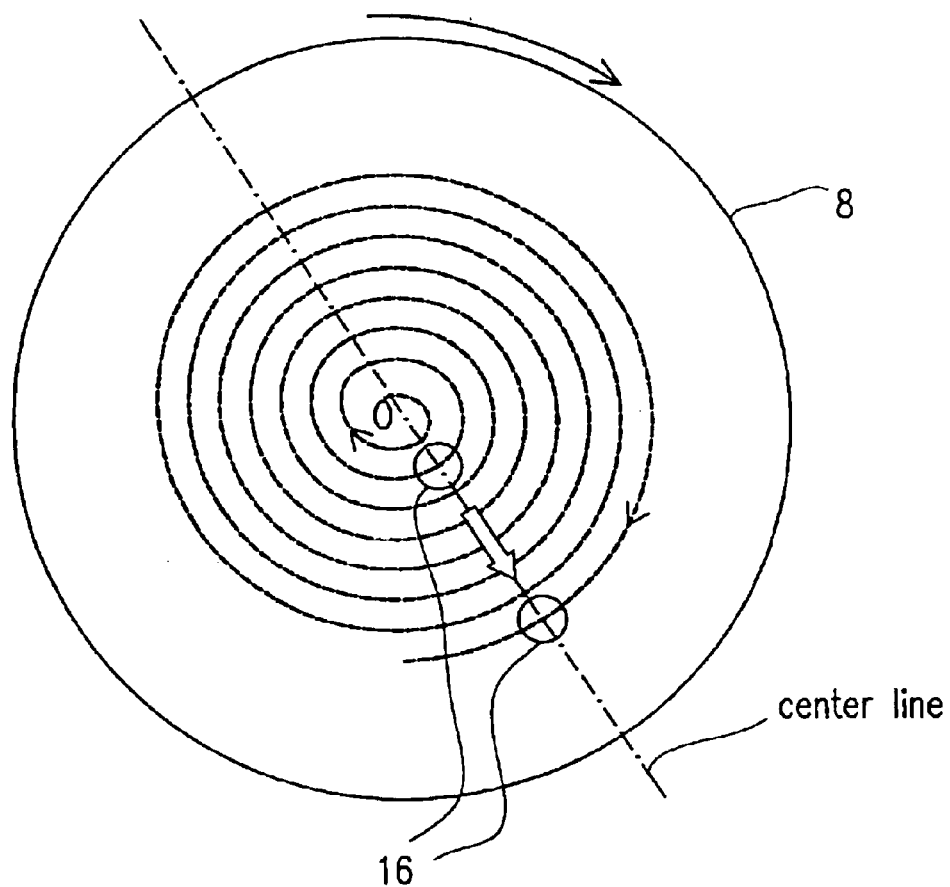
FIG. 3 shows another trail of the light spot 16 on the surface of the object 8.

FIG. 3 shows another trail of the light spot 16 on the surface of the object 8. In the case where the object 8 has a circular shape, such as an optical disc, it is desirable that the light beam emitted from the light source 4 onto the object 8 is translated along a center line which passes through point O by the movement section 9 while the object 8 is rotated by rotation means (not shown), such that the light spot 16 moves as shown by the broken line in FIG. 3. Herein, point O in FIG. 3 is the center point of the object 8.

Figure 4:
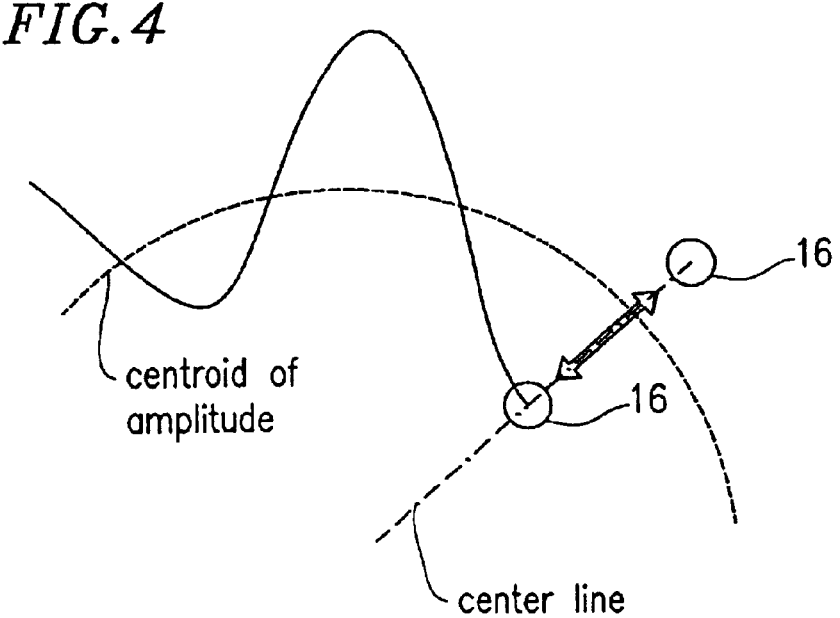
FIG. 4 shows still another trail of the light spot 16 on the surface of the object 8.

FIG. 4 shows still another trail of the light spot 16 on the surface of the object 8. A scanning method illustrated in FIG. 4 is effective in the case where the object 8 has a circular shape (e.g., as shown in FIG. 3), such as an optical disc. In the case of FIG. 4, the vibration section 102 vibrates the converging section 5 at a desired amplitude, in addition to the spiral movement of the light spot 16 shown in FIG. 3 (i.e., rotation of the object 8 and movement of the light beam by the movement section 9). As a result, the light spot 16 forms a trail which oscillates in a direction perpendicular to the rotation direction of the object 8. Due to such a trail of the light spot 16 shown in FIG. 4, the time spent for scanning the object 8 is shortened.

Figure 5A:
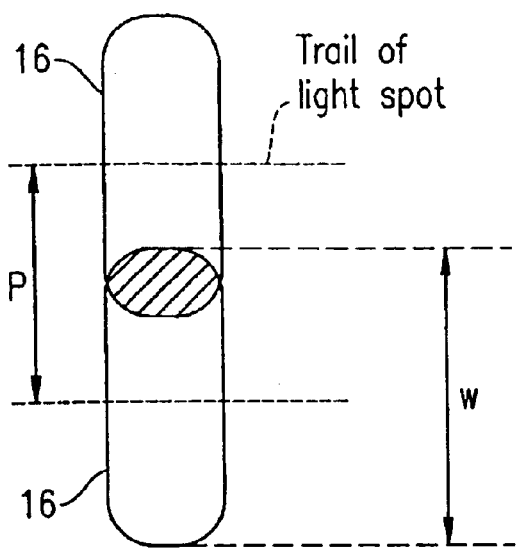
FIG. 5(a) shows a relationship between a scanning pitch p and a spot width w of the light spot 16.
Figure 5B:
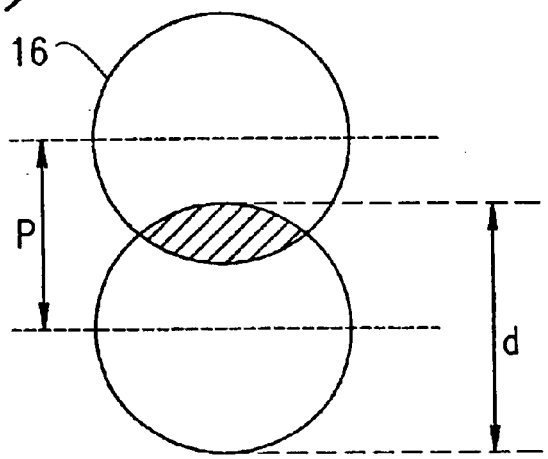
FIG. 5(b) shows a relationship between the scanning pitch p and a spot diameter d of the light spot 16.

FIG. 5(a) shows a relationship between a scanning pitch p and a spot width w of the light spot 16. FIG. 5(b) shows a relationship between the scanning pitch p and a spot diameter d of the light spot 16. In the case where the light spot 16 has a rectangular shape, it is desirable that the scanning pitch p and the spot width w satisfy the relationship p<w as shown in FIG. 5(a), i.e., the trail of the light spot 16 has an overlapped portion (a hatched portion in FIG. 5(a)). With such an arrangement, the entire examination region on the surface of the object 8 can be scanned with the light spot 16, and accordingly, the detection accuracy increases. Also in the case where the light spot 16 has a circular shape, it is desirable that the scanning pitch p and the spot diameter d satisfies the relationship p<d as shown in FIG. 5(b), i.e., the trail of the light spot 16 has a overlapped portion (a hatched portion in FIG. 5(b)). In the case where the surface of the object 8 is scanned for a foreign substance in a quick and simple manner, the relationship between the scanning pitch p and spot width w (or spot diameter d) may be p>w (or p>d).

Referring again to FIG. 1, the light detection portion 7 receives a light beam reflected by the surface of the object 8 and transmitted through the converging section 5 and the beam splitter 6, and converts the received light into an electric current signal which indicates the quantity of the received light. The light detection portion 7 further includes a first light detection portion 7A and a second light detection portion 7B. The first light detection portion 7A and the second light detection portion 7B generate a first electric current signal (first light detection signal) $I_A$ and a second electric current signal (second light detection signal) $I_B$, respectively. The first light detection portion 7A and the second light detection portion 7B maybe, for example, any photoelectric conversion element, such as a photodiode, a CCD, etc.

Figure 6:
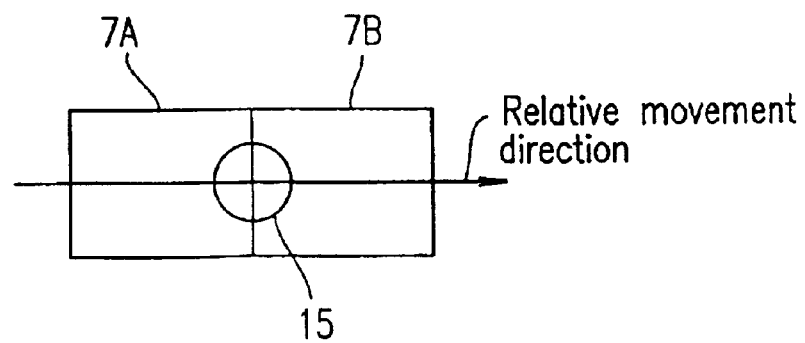
FIG. 6 shows an arrangement of a first light detection portion 7A and a second light detection portion 7B.

FIG. 6 shows the arrangement of the first light detection portion 7A and the second light detection portion 7B. The first light detection portion 7A and the second light detection portion 7B are preferably arranged such that a light beam 15 reflected by the object 8 is first received by the first light detection portion 7A, and then received by the second light detection portion 7B. With such an arrangement, the perimeter of a foreign substance on the object 8 can be accurately identified.

Referring to FIG. 1, the signal generation section 2 generates, from the first electric current signal $I_A$ and the second electric current signal $I_B$ which are generated in the light detection section 1, a difference voltage signal for identifying the perimeter of a foreign substance on the surface of the object 8. The signal generation section 2 includes a current-voltage converter (I-V converter) 10 and a difference signal generation section 11.

The I-V converter 10 converts an electric current signal generated by the light detection portion 7 into a voltage signal. The I-V converter 10 includes a first I-V converter 10A and a second I-V converter 10B. The first I-V converter 10A receives the first electric current signal $I_A$ generated by the first light detection portion 7A and generates a first voltage signal $V_A$. The second I-V converter 10B receives the second electric current signal $I_B$ generated by the second light detection portion 7B and generates a second voltage signal $V_B$. In embodiment 1, the electric current signal generated by the light detection portion 7 is used as the light detection signal. However, a voltage signal generated by the I-V converter 10 may be used as the light detection signal.

The difference signal generation section 11 generates a difference voltage signal (difference signal) $V_A-V_B$ from the first voltage signal $V_A$ and the second voltage signal $V_B$ which are generated by the I-V converter 10.

The determination section 3 compares the difference voltage signal $V_A-V_B$ generated by the signal generation section 2 and a reference voltage signal (reference value) $V_{ref}$ so as to determine the existence range of the foreign substance on the object 8. The determination section 3 includes a perimeter signal generation section 103 and a foreign substance determination section 14.

The perimeter signal generation section 103 includes a first comparator 12A, a second comparator 12B, and a reference voltage generator 13. The reference voltage generator 13 includes a first reference voltage generator 13A and a second reference voltage generator 13B.

The first reference voltage generator 13A generates a first reference voltage (first reference value) $V_{refA}$. The second reference voltage generator 13B generates a second reference voltage (second reference value) $V_{refB}$. The first and second reference voltage generators 13A and 13B are set such that the absolute value of the first reference voltage $V_{refA}$ is equal to that of the second reference voltage $V_{refB}$. The first reference voltage $V_{refA}$ and the second reference voltage $V_{refB}$ vary according to the average value of the quantity of light reflected from the surface of the object on which a foreign substance does not exist. According to the present invention, in order to obtain the reference voltage, an average value of the light quantity calculated from a theoretical reflectance of an object, which is used in a conventional technique, is not used. An average value of the light quantity measured under a normal condition for using the foreign substance existence range determination apparatus 100 is used so as to obtain the reference value. That is, the reference voltage is variable, and therefore, a suitable reference voltage can be set according to the environment in which the foreign substance existence range determination apparatus 100 is used. Since the reference voltage set according to the environment in which the foreign substance existence range determination apparatus 100 is used for detection of a foreign substance, the foreign substance can be accurately detected. It is preferable that the reference voltage is set for each measurement process. In such a case, the detection accuracy for detecting a foreign substance is improved. The average value of the light quantity can be obtained by using any of various averaging operations, such as an arithmetic mean, a moving average, a portion average, or the like.

The first comparator 12A and the second comparator 12B may be any comparator. The first comparator 12A compares the difference voltage signal $V_A-V_B$ and the first reference voltage $V_{refA}$. The second comparator 12B compares the difference voltage signal $V_A-V_B$ and the second reference voltage $V_{refB}$. From the results of comparison in the first comparator 12A and the second comparator 12B, a perimeter signal which indicates the perimeter of the foreign substance is generated.

The foreign substance determination section 14 uses the perimeter signal generated by the perimeter signal generation section 103 to determine the existence range of the foreign substance. The foreign substance determination section 14 may be, for example, a flip flop circuit.

Figure 7:
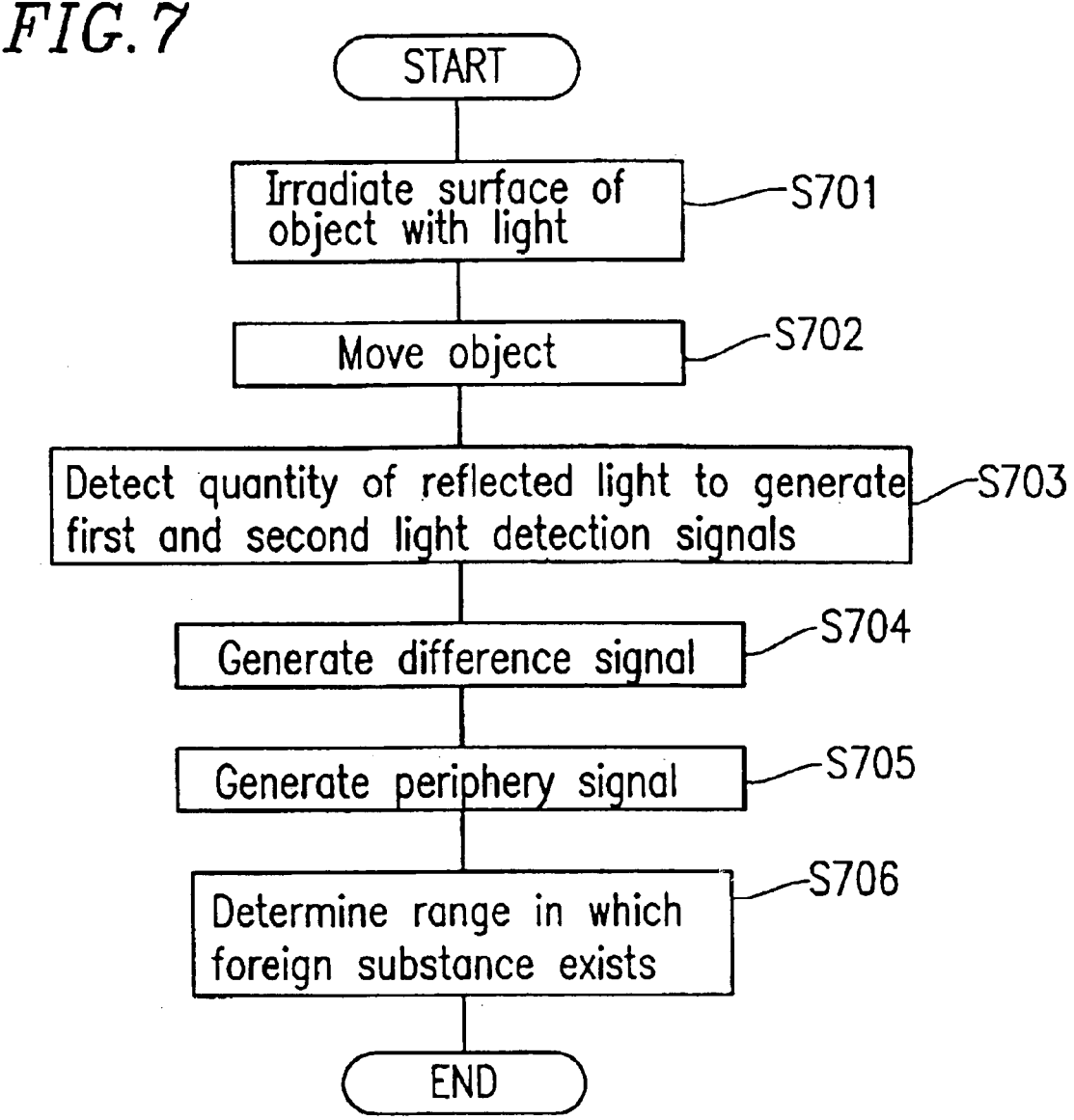
FIG. 7 is a flowchart which illustrates a method for determining an existence range of a foreign substance using the foreign substance existence range determination apparatus 100 according to embodiment 1 of the present invention.

FIG. 7 is a flowchart which illustrates a method for determining an existence range of a foreign substance using the foreign substance existence range determination apparatus 100 according to embodiment 1 of the present invention.

Figure 8:
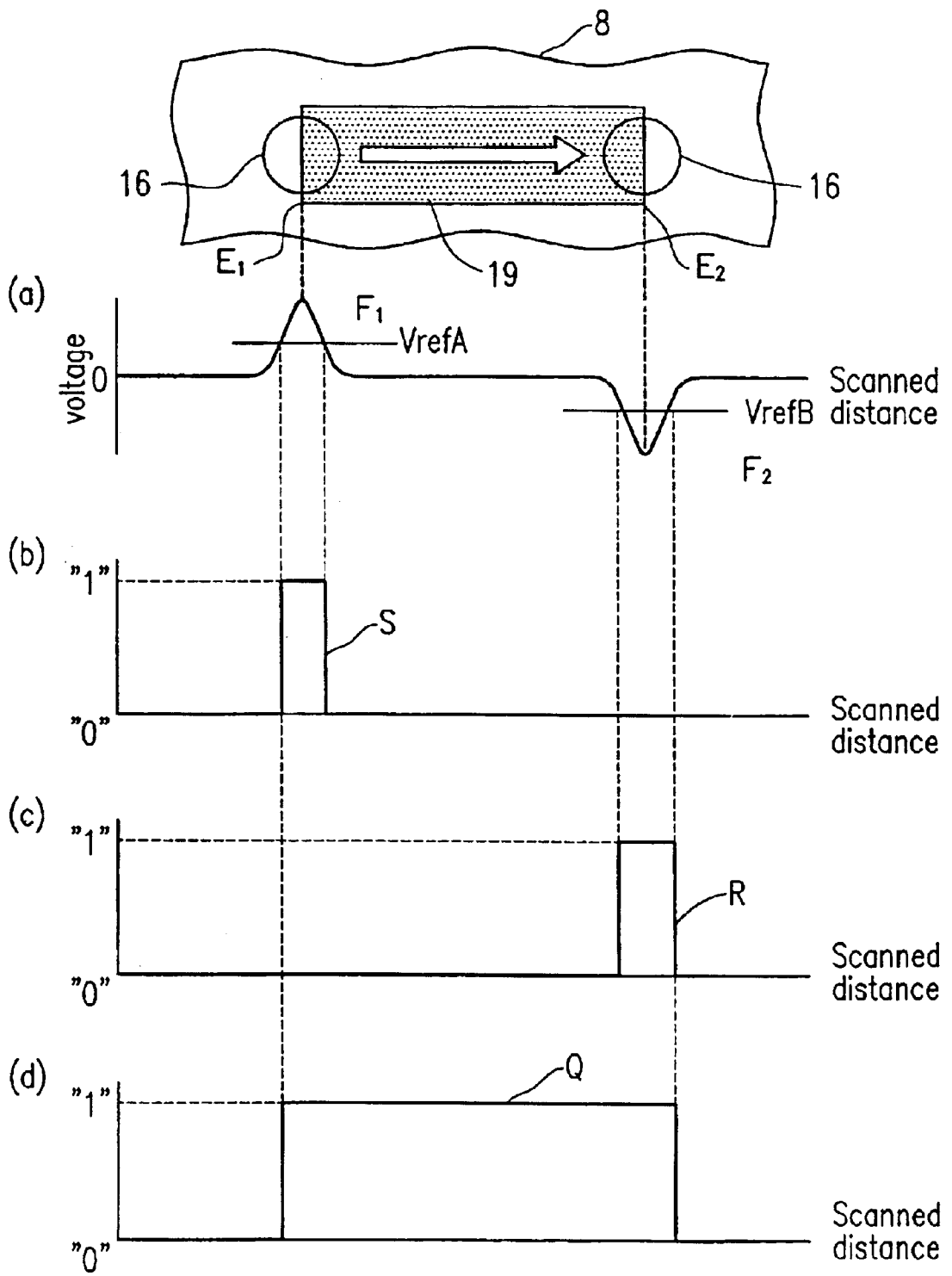
FIG. 8 shows signals generated by the various components in the foreign substance existence range determination apparatus 100 according to embodiment 1 of the present invention.

FIG. 8 shows signals generated by various components in the foreign substance existence range determination apparatus 100 according to embodiment 1 of the present invention.

The method for determining an existence range of a foreign substance 19 on the surface of the object 8 (FIG. 1) is now described in a step-by-step manner with reference to FIGS. 7 and 8. Herein, consider a case where the rectangular foreign substance 19 attached to the object 8 has reflectance $n_{var}$ which is smaller than the reflectance of the object 8, $n_{ob}$.

Step S701: The light source 4 (FIG. 1) emits a light beam toward the object 8. The light beam emitted from the light source 4 is reflected by the beam splitter 6 (FIG. 1), and converged by the converging section 5 (FIG. 1), so as to form a light spot 16 (FIG. 8) on the surface of the object 8.

Step S702: The object 8 is moved with respect to the light beam, such that the light spot 16 moves as shown by the broken line in FIG. 2 (arrow in FIG. 8) for scanning the surface of the object 8.

Step S703: The first light detection portion 7A and the second light detection portion 7B receive a light beam reflected by the surface of the object 8 and transmitted through the converging section 5 and the beam splitter 6. The first light detection portion 7A and the second light detection portion 7B respectively generate a first electric current signal $I_A$ and a second electric current signal $I_B$, each of which indicate the quantity of the received light.

Step S704: The first electric current signal $I_A$ and the second electric current signal $I_B$ generated by the light detection portion 7 are respectively converted to a first voltage signal $V_A$ and a second voltage signal $V_B$ by the I-V converter 10. In the difference signal generation section 11, a difference voltage signal $V_A-V_B$ is generated from the first voltage signal $V_A$ and the second voltage signal $V_B$. The thus-generated difference voltage signal is shown in section (a) of FIG. 8. In section (a) of FIG. 8, the horizontal axis represents the scanned distance, and the vertical axis represents voltage.

When the light spot 16 reaches a first perimeter portion $E_1$ of the foreign substance 19, the quantity of light reflected from the object 8 sharply decreases. Thus, the first voltage signal $V_A$, which is generated by the first light detection portion 7A, and the second voltage signal $V_B$, which is generated by the second light detection portion 7B, has the relationship $V_A>V_B$. As a result, pulse-shaped waveform $F_1$ is obtained.

Between the first perimeter portion $E_1$ and a second perimeter portion $E_2$ of the foreign substance 19, the quantity of light reflected from the object 8 is constant. Thus, the first voltage signal $V_A$, which is generated by the first light detection portion 7A, and the second voltage signal $V_B$, which is generated by the second light detection portion 7B, has the relationship $V_A=V_B$. As a result, a flat waveform is obtained.

When the light spot 16 reaches the second perimeter portion $E_2$ of the foreign substance 19, the quantity of light reflected from the object 8 sharply increases. Thus, the first voltage signal $V_A$, which is generated by the first light detection portion 7A, and the second voltage signal $V_B$, which is generated by the second light detection portion 7B, has the relationship $V_A<V_B$. As a result, pulse-shaped waveform $F_2$ is obtained.

Step S705: The difference voltage signal generated at step S704 and the reference voltage are compared to generate perimeter signals which respectively indicate the first perimeter portion $E_1$ and a second perimeter portion $E_2$ of the foreign substance 19.

In the first comparator 12A, the difference voltage signal $V_A-V_B$ and the first reference voltage $V_{refA}$ generated by the first reference voltage generator 13A are compared. If the difference voltage signal $V_A-V_B$ and the first reference voltage $V_{refA}$ satisfy the relationship $V_A-V_B>V_{refA}$, the first comparator 12A outputs "1" which indicates the presence of the foreign substance 19. (If otherwise, the first comparator 12A outputs "0" which indicates the absence of a foreign substance.) The thus-output digital signal waveform S is shown in section (b) of FIG. 8. The digital signal waveform S indicates the first perimeter portion $E_1$ of the foreign substance 19. In section (b) of FIG. 8, the horizontal axis represents the scanned distance, and the vertical axis represents a binary value (i.e., "0" or "1").

Similarly, in the second comparator 12B, the difference voltage signal $V_A-V_B$ and the second reference voltage $V_{refB}$ generated by the second reference voltage generator 13B are compared. If the difference voltage signal $V_A-V_B$ and the second reference voltage $V_{refB}$ satisfy the relationship $V_A-V_B<V_{refB}$, the second comparator 12B outputs "1" which indicates the presence of the foreign substance 19. (If otherwise, the first comparator 12B outputs "0" which indicates the absence of a foreign substance.) The thus-output digital signal waveform R is shown in section (c) of FIG. 8. The digital signal waveform R indicates the second perimeter portion $E_2$ of the foreign substance 19. In section (c) of FIG. 8, the horizontal axis represents the scanned distance, and the vertical axis represents a binary value (i.e., "0" or "1").

Step S706: The perimeter signals S and R generated at step S705 are used to determine a range on the surface of the object 8 in which the foreign substance 19 exists. The foreign substance determination section 14, which is a flip flop circuit, for example, processes the perimeter signals S and R to output "1", which indicates the presence of the foreign substance 19, and "0", which indicates the absence of the foreign substance 19. The thus-output digital signal waveform Q is shown in section (d) of FIG. 8. The digital signal waveform Q is a signal such that the value between the digital signal waveform S of section (b) and the digital signal waveform R of section (a) is "1". In section (d) of FIG. 8, the horizontal axis represents the scanned distance, and the vertical axis represents a binary value (i.e., "0" or "1"). In this way, the existence range of the foreign substance 19 on the surface of the object 8 can be determined.

Even in the case where a foreign substance attached to the object 8 has reflectance $n_{var}$ which is greater than the reflectance $n_{ob}$ of the object 8, the foreign substance can be detected in the same manner.

Next, consider a case where the reflectance $n_{var}$ of a foreign substance is substantially the same as the reflectance $n_{ob}$ of the object 8.

FIG. 9 shows a difference voltage signal generated from a light beam having a wavefront aberration, and a difference voltage signal generated from a light beam not having a wavefront aberration, in the foreign substance existence range determination apparatus 100 according to embodiment 1 of the present invention.

In FIG. 9, assume that the reflectance $n_{var}$ of a foreign substance 21 is substantially equal to the reflectance $n_{ob}$ of the object 8. In such a case, it is desirable for determining the existence range of the foreign substance 21 that a light beam emitted onto the surface of the object 8 has a wavefront aberration. In section (a) of FIG. 9, glass 22 (refractive index=1.5 to 1.6) is provided between the converging section 5 and the object 8 such that a light beam emitted onto the surface of the object 8 does not have a wavefront aberration. In section (b) of FIG. 9, the glass 22 is removed from the structure shown in section (a), and a light beam emitted onto the surface of the object 8 has a wavefront aberration. The converging section 5 is located in the vicinity the object 8 such that distance D' between the converging section 5 and the object 8 (in the case where the light beam is not focused on the object 8) is shorter than distance D (in the case where the light beam is focused on the object 8) in FIG. 1 (i.e., D'<D). With such an arrangement, the light beam emitted onto the surface of the object 8 has a wavefront aberration. Alternatively, the object 8 maybe located in the vicinity of the converging section 5 such that the light beam is not focused on the object 8.

In the case where the light beam emitted onto the surface of the object 8 does not have a wavefront aberration as shown in section (a) of FIG. 9, the obtained difference voltage signal $V_A-V_B$ has a narrow pulse width, and the amplitude of the pulse is lower than reference voltage $V_{ref}$. When such a difference voltage signal $V_A-V_B$ is compared with reference voltage $V_{ref}$, the perimeter signal generation section 103 (FIG. 1) outputs "0" which indicates that there is no foreign substance on the surface of the object 8. Thus, the foreign substance 21 cannot be detected.

In the case where the light beam emitted onto the surface of the object 8 has a wavefront aberration as shown in section (b) of FIG. 9, the obtained difference voltage signal $V_A-V_B$ has a pulse amplitude which exceeds reference voltage $V_{ref}$. When such difference voltage signal $V_A-V_B$ is compared with reference voltage $V_{ref}$, the perimeter signal generation section 103 (FIG. 1) outputs "1" which indicates that there is a foreign substance on the surface of the object 8. Thus, the foreign substance 21 can be correctly detected.

A desirable degree of the wavefront aberration is such that the standard deviation of the wavefront aberration is 0.07 or more times the wavelength of monochromic light.

By using light having a wavefront aberration, a foreign substance having substantially the same reflectance as that of an object can be correctly detected. Reasons for this are described below.

In the case of a light beam not having a wavefront aberration, the light amplitude distribution over the surface of the object 8 on which the foreign substance 21 is not attached and the light amplitude distribution over an aperture plane of the converging section 5 have a relationship according to Fourier conversion. For example, the light amplitude distribution over the surface of the object 8 is represented as "$\exp\{-(x/a)^2\}$" in the one-dimensional representation (where x is a coordinate on the surface of the object 8 taken along the scanning direction of the light spot, and a denotes a coefficient associated with a radius of light distribution). On the other hand, the light amplitude distribution over an aperture plane of the converging section 5 is represented as "$a\times\exp\{-(au/2)^2\}$" in the one-dimensional representation (where u denotes a coordinate on the aperture plane).

In the case where the foreign substance 21 is attached on the surface of the object 8, a portion of the light amplitude distribution over the surface of the object 8 on which the foreign substance 21 is not attached is shielded. For example, in the case where the foreign substance 21 is attached to the surface of the object 8 in the range of x>0, the light amplitude distribution in the range of x>0 is 0, whereas the light amplitude distribution in the range of x≦0 is $\exp\{-(x/a)^2\}$. The light amplitude distribution is approximately represented by "$\exp\{-(2x/a+1)^2\}$" ... ①. By performing Fourier conversion on, expression ①, the light amplitude distribution over an aperture plane of the converging section 5 is represented as "$a/2\times\exp\{-(au/4)^2\}\times\exp(iau/2)$ (where i represents a complex unit)" ... ②. The light detection portion 7 receives a light beam having the light amplitude distribution represented by expression ②, and generates an electric current signal which indicates the quantity of the received light. The light quantity, i.e., light intensity, is the second power of the absolute value of the light amplitude. Thus, the light quantity obtained from expression ② is $(a/2)^2\times\exp\{-(au/4)^2\}$ ... ③. It is appreciated from expression ③ that the light quantity distribution over the aperture plane of the converging section 5 exhibits a symmetrical distribution such that the light quantity distribution in the positive coordinate range (u>0) over the aperture plane is symmetrical with that in the negative coordinate range (u<0). Therefore, no difference occurs between the light quantity at a positive coordinate on the aperture plane of the converging section 5 and the light quantity at a negative coordinate on the aperture plane of the converging section 5. That is, a difference voltage signal which indicates a perimeter portion of a foreign substance is not generated.

However, in the case of a light beam having a wavefront aberration, the light amplitude distribution over the surface of the object 8 and the light amplitude distribution over an aperture plane of the converging section 5 do not have Fourier conversion relationship. As a result, the light amplitude distribution over an aperture plane of the converging section 5 (i.e., light quantity distribution) exhibits an asymmetrical distribution such that the light quantity distribution in the positive coordinate range (u>0) over the aperture plane is asymmetrical with that in the negative coordinate range (u<0). Accordingly, a difference voltage signal is generated.

As described above, according to embodiment 1, a difference signal $V_A-V_B$, which indicates a difference between a first light detection signal $I_A$ and a second light detection signal $I_B$, and a reference value $V_{ref}$ are used to determine an existence range of a foreign substance. In the case where a first electric current signal $I_A$ in the conventional foreign substance detection apparatus 1500 and a first light detection signal $I_A$ in the foreign substance existence range determination apparatus 100 of the present invention are the same as a second electric current signal $I_B$ in the conventional foreign substance detection apparatus 1500 and a second light detection signal $I_B$ in the foreign substance existence range determination apparatus 100 of the present invention, respectively, the signal quality of a difference voltage signal $V_A-V_B$ is higher than that of a sum voltage signal $V_A+V_B$. This is because noise is cancelled by generating a difference signal.

Further, according to the present invention, a reference voltage is set appropriately according to an environment in which the foreign substance existence range determination apparatus 100 is used. Thus, a large margin can be secured in the reference voltage for a variation in the quantity of light detected by a light detection section. Thus, a foreign substance can be accurately detected.

Furthermore, according to the present invention, a light converging section is provided such that light emitted onto an object has a wavefront aberration. As a result, even a foreign substance having substantially the same reflectance as that of an object can be readily detected.

Further still, according to the present invention, a foreign substance can be detected without using a special environment (e.g., a clean room) or a high-precision, complicated control apparatus. Thus, the present invention is cost efficient.

Embodiment 2

Figure 10:
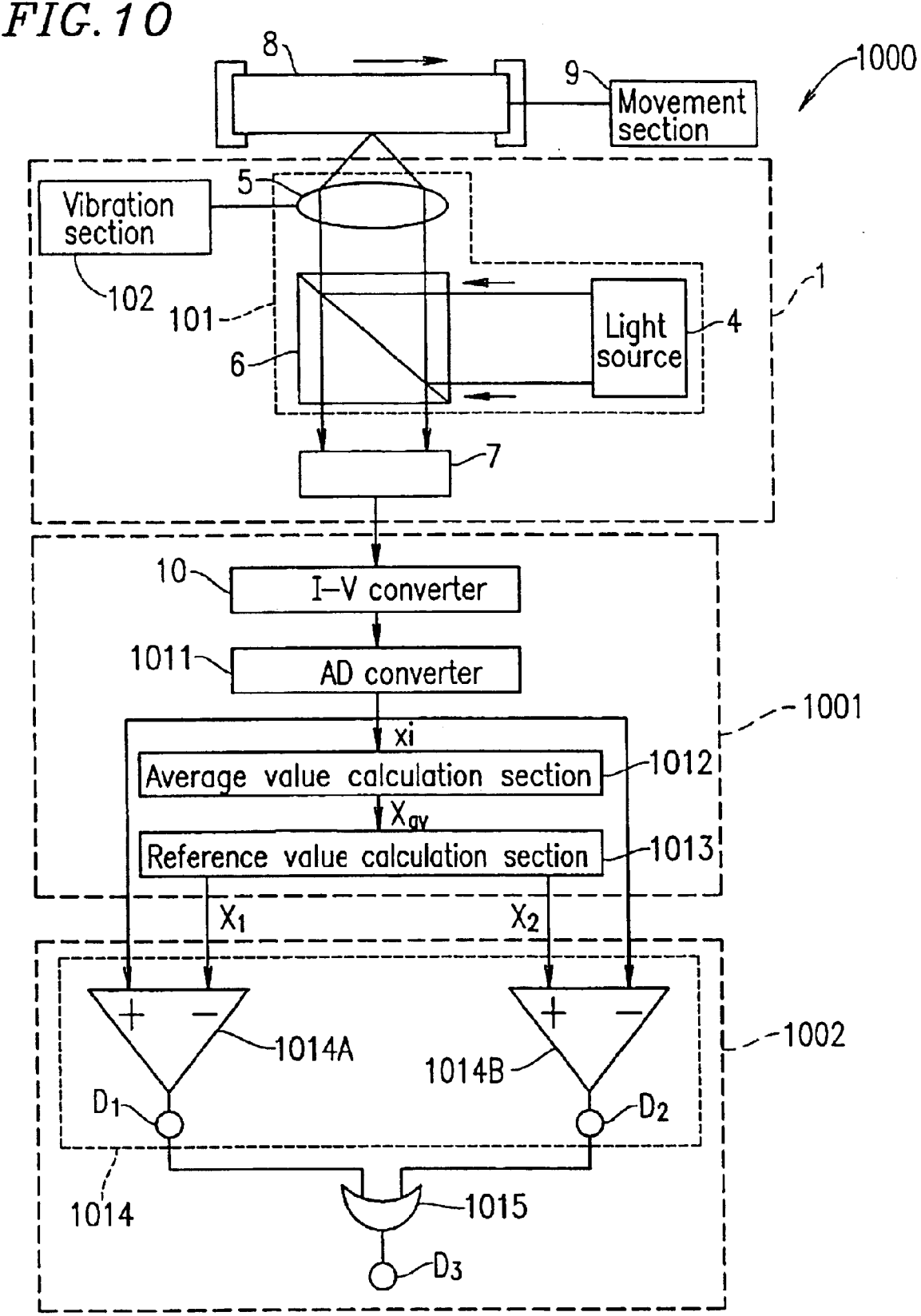
FIG. 10 shows a structure of a foreign substance existence range determination apparatus 1000 according to embodiment 2 of the present invention.

FIG. 10 shows a structure of a foreign substance existence range determination apparatus 1000 according to embodiment 2 of the present invention. In FIG. 10, like elements are indicated by like reference numerals used in FIG. 1, and detailed descriptions thereof are omitted. The foreign substance existence range determination apparatus 1000 optically determines a range on a surface of an object 8 in which a foreign substance exists. The foreign substance existence range determination apparatus 1000 includes a light detection section 1, a signal generation section 1001, and a determination section 1002. The object 8 may be, for example, an optical disc, a magnetic disc, etc.

The light detection section 1 of embodiment 2 is the same as that of embodiment 1 except that a light detection portion 7 of embodiment 2 does not include a first light detection portion 7A and a second light detection portion 7B, and detailed descriptions thereof are omitted. Further, also in embodiment 2, the scanning methods of a light spot, which have been described in embodiment 1 with reference to FIGS. 2 through 5, are applicable.

The signal generation section 1001 generates, from an electric current signal generated by the light detection section 1, a reference voltage (reference value) used for determining presence/absence of a foreign substance on the surface of the object 8. The signal generation section 1001 includes a current-voltage converter (I-V converter) 10, an analog-digital converter (AD converter) 1011, an average value calculation section 1012, and a reference value calculation section 1013. The I-V converter 10 of embodiment 2 is the same as the I-V converter 10 of FIG. 1. The I-V converter 10 converts an electric current signal (light detection signal) to an analog voltage signal.

The AD converter 1011 converts an analog voltage signal generated by the I-V converter 10 to a digital voltage signal xi. In embodiment 2, the electric current signal generated by the light detection portion 7 is used as the light detection signal. However, a digital voltage signal generated by the I-V converter 10 may be used as the light detection signal.

The average value calculation section 1012 calculates an average voltage (average value) $X_{av}$ of the digital voltage signal xi generated by the AD converter 1011. The average value calculation section 1012 maybe, for example, any calculation device, such as digital signal processor (DSP), a central processing unit (CPU), or the like.

Figure 11A:
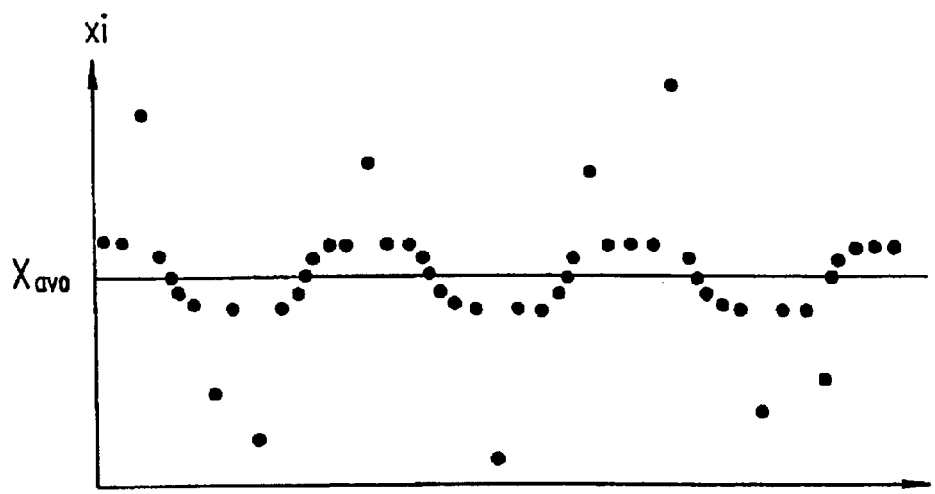
FIGS. 11(a) and 11(b) illustrate calculation of an average voltage $X_{av}$ in an average value calculation section 1012 of the foreign substance existence range determination apparatus 1000.
Figure 11B:
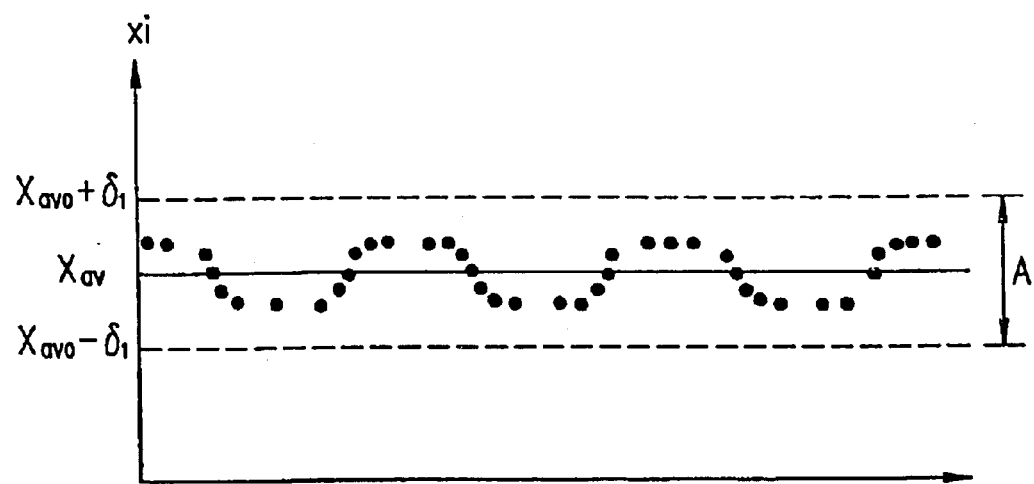

FIGS. 11(a) and 11(b) illustrates calculation of the average voltage $X_{av}$ in the average value calculation section 1012. The average voltage (average value) $X_{av}$ is obtained by averaging a sampled voltage signal xi using a calculation formula selected from various averaging operation formulas, such as an arithmetic mean, a moving average, a portion average, or the like. The averaging calculation formula may be selected appropriately according to the purpose of detection (e.g., the type of a foreign substance to be detected, etc.).

Next, a procedure for obtaining the average voltage $X_{av}$ is described in detail with reference to FIGS. 11(a) and 11(b).

At the first step, all sampled values of the digital voltage signal xi (population) is averaged using any averaging operation formula so as to calculate an average voltage $X_{av0}$ (FIG. 11(a)). Next, only the digital voltage signal xi within a region which does not exceed positive and negative standard deviations $\pm\delta_1$ (i.e., $X_{av0}-\delta_1 \leq xi \leq X_{av0}+\delta_1$) is extracted. That is, only a portion of the digital voltage signal xi which is in a range A of FIG. 11(b) is extracted. Then, only values of the digital voltage signal xi which is in the range A are averaged to calculate an average voltage $X_{av}$ using any averaging operation formula. In this way, the average voltage $X_{av}$, which is used for determining an existence range of a foreign substance, is obtained from the sampled voltage signal xi.

As described above, the average voltage $X_{av}$ is obtained by averaging some of the values of the sampled voltage signal xi which are in a specific range. Thus, a reference voltage (reference value) is accurately generated in a subsequent step, and detection accuracy for detecting a foreign substance can be improved. The sampled voltage signal xi (population), which is used for obtaining the average voltage $X_{av}$, may be a voltage signal for the entire surface of the object 8 or may be a voltage signal for only a portion of the surface of the object 8. In the case where the population is a voltage signal for the entire surface of the object 8, the detection accuracy for detecting a foreign substance is improved. Further, the population is a voltage signal for a portion of the surface of the object 8, the average voltage can be calculated in a simple and quick manner. Sampling for obtaining the average voltage $X_{av}$ can be achieved by measuring the quantity of light reflected by the surface of the object 8 onto which no foreign substance is attached under a normal environment for using the foreign substance existence range determination apparatus 1000.

The reference value calculation section 1013 uses a function where the average voltage $X_{av}$ calculated in the average value calculation section 1012 is a variable, so as to calculate a first reference voltage (first reference value) $X_1$ and a second reference voltage (second reference value) $X_2$. The reference value calculation section 1013 may be any arithmetic operation device which can perform numeric arithmetic (so-called number crunching) according to an arithmetic operation formula used for calculating the first reference value $X_1$ and the second reference value $X_2$, such as a coefficient device, a multiplier, a divider, an adder, a subtracter, etc. The first reference value $X_1$ is used for detecting an foreign substance whose reflectance $n_{var}$ is larger than the reflectance $n_{ob}$ of the object 8 ($n_{ob}<n_{var}$). On the other hand, the second reference value $X_2$ is used for detecting an foreign substance whose reflectance $n_{var}$ is smaller than the reflectance $n_{ob}$ of the object 8 ($n_{ob}>n_{var}$)

The first reference value $X_1$ and the second reference value $X_2$ are calculated using an arithmetic operation formula selected from a group of expressions ④–⑥:

$$X_1 = X_{av} \cdot (1+\beta_1), X_2 = X_{av} \cdot (1-\alpha_1); \quad ④$$

$$X_1 = X_{av}/(1-\alpha_2), X_2 = X_{av}/(1+\beta_2); \quad ⑤$$

$$X_1 = X_{av}+\beta_3, X_2 = X_{av}-\alpha_3, \quad ⑥$$

where $X_{av}$ is an average value; $\alpha_1, \alpha_2, \alpha_3, \beta_1, \beta_2, \beta_3 > 0$; and each of $\alpha_1, \alpha_2, \alpha_3, \beta_1, \beta_2$, and $\beta_3$ is a constant value. The constant values $\alpha_1, \alpha_2, \alpha_3, \beta_1, \beta_2$, and $\beta_3$ are set according to the measurement accuracy of the light detection section 1. For example, in the case where expression ④ or ⑤ is used, the accuracy for detecting a foreign substance is high. In the case where expression ⑥ is used, the structure of the reference value calculation section 1013 can be simplified. By setting the average value and the first and second reference values for each measurement process, the detection accuracy for detecting a foreign substance is improved.

FIG. 12 illustrates an arithmetic process performed in the determination section 1002 included in the foreign substance existence range determination apparatus 1000.

The determination section 1002 compares the voltage signal xi generated in the signal generation section 1001 with the first reference value $X_1$ or second reference value $X_2$, so as to determine an existence range of a foreign substance on the object 8. The determination section 1002 includes a comparison signal generation section 1014 and a foreign substance determination section 1015. The comparison signal generation section 1014 and the foreign substance determination section 1015 are described below with reference to FIGS. 10 and 12.

The comparison signal generation section 1014 includes a first comparator 1014A and a second comparator 1014B. The first comparator 1014A compares the voltage signal xi generated by the AD converter 1011 with the first reference voltage $X_1$. The second comparator 1014B compares the voltage signal xi generated by the AD converter 1011 with the second reference voltage $X_2$.

If the first reference voltage $X_1$ and the voltage signal xi satisfy the relationship $X_1<xi$, the first comparator 1014A outputs "1" which indicates the presence of a foreign substance. If otherwise, the first comparator 1014A outputs "0" which indicates the absence of a foreign substance. (Herein, the value "1" or "0" output by the first comparator 1014A is referred to as a first comparison signal $D_1$.) That is, if there is a foreign substance whose reflectance $n_{var}$ is larger than the reflectance $n_{ob}$ of the object 8 ($n_{ob}<n_{var}$), the first comparator 1014A outputs "1". If such a foreign substance does not exist, the first comparator 1014A outputs "0".

If the second reference voltage $X_2$ and the voltage signal xi satisfy the relationship $X_2>xi$, the second comparator 1014B outputs "1" which indicates the presence of a foreign substance. If otherwise, the second comparator 1014B outputs "0" which indicates the absence of a foreign substance. (Herein, the value "1" or "0" output by the second comparator 1014B is referred to as a second comparison signal $D_2$.) That is, if there is a foreign substance whose reflectance $n_{var}$ is smaller than the reflectance $n_{ob}$ of the object 8 ($n_{ob}>n_{var}$), the second comparator 1014B outputs "1". If such a foreign substance does not exist, the second comparator 1014B outputs "0".

The foreign substance determination section 1015 uses the first comparison signal $D_1$ and the second comparison signal $D_2$, which are generated by the comparison signal generation section 1014, are used to generate a signal $D_3$ which indicates the existence range of a foreign substance. The foreign substance determination section 1015 may be, for example, an OR gate circuit, a DSP, or a CPU. If the first comparison signal $D_1$ and the second comparison signal $D_2$ satisfy the relationship $D_1 \cup D_2=1$, the foreign substance determination section 1015 outputs as signal $D_3$, "1", which indicates the presence of a foreign substance. If otherwise, the foreign substance determination section 1015 outputs as signal $D_3$, "0", which indicates the absence of a foreign substance. That is, the foreign substance determination section 1015 outputs "1" when there is a foreign substance, and "0" when there is not a foreign substance, regardless of the relationship between the reflectance $n_{ob}$ of the object 8 and the reflectance $n_{var}$ of a foreign substance.

FIG. 13 is a flowchart which illustrates a method for determining an existence range of a foreign substance using the foreign substance existence range determination apparatus 1000 according to embodiment 2 of the present invention.

Figure 14:
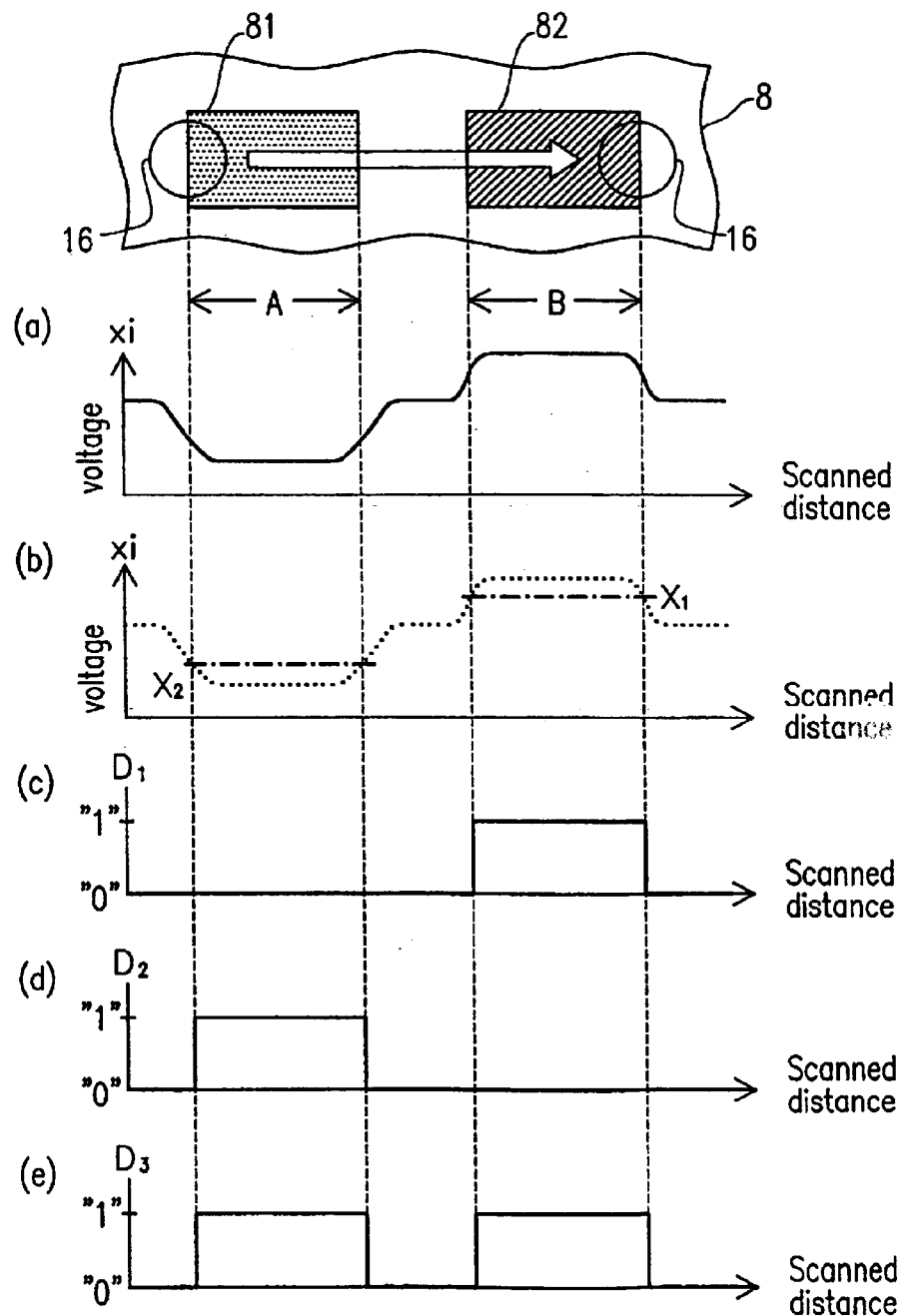
FIG. 14 shows signals generated by the various components in the foreign substance existence range determination apparatus 1000 according to embodiment 2 of the present invention.
Figure 15:
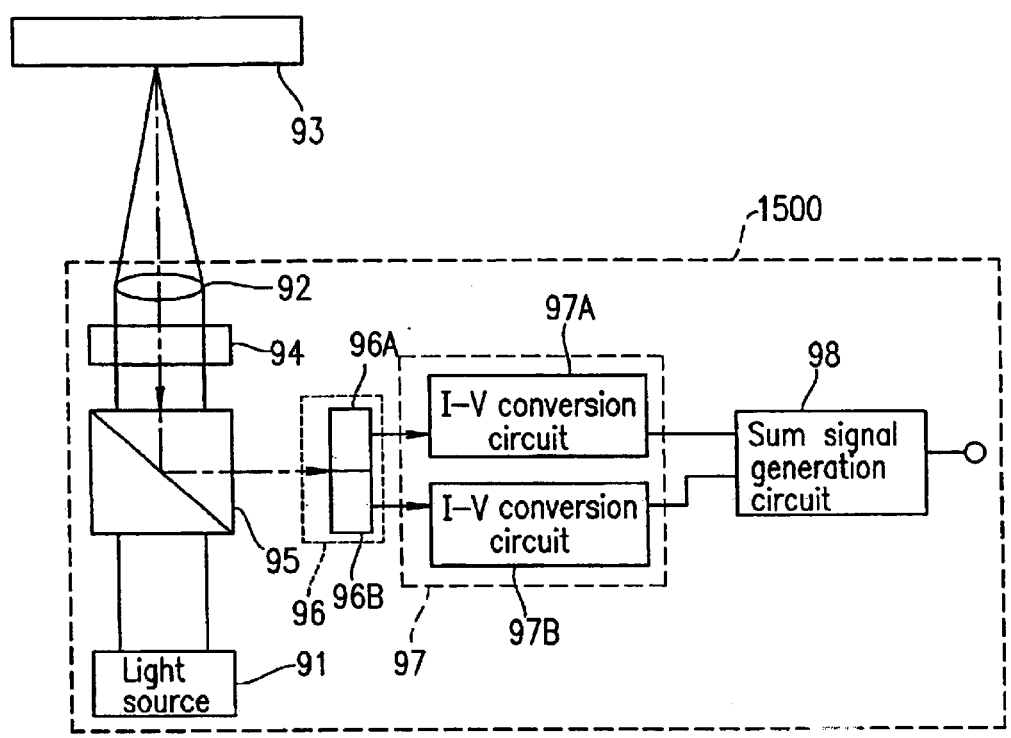
FIG. 15 shows a structure of a conventional foreign substance detection apparatus 1500 for use with an optical disc 93.

FIG. 14 shows signals generated in the foreign substance existence range determination apparatus 1000 according to embodiment 2 of the present invention.

The method for determining an existence range of foreign substances 81 and 82 on the surface of the object 8 is now described in a step-by-step manner with reference to FIGS. 13 and 14. Herein, consider a case where the rectangular foreign substances 81 and 82 are attached to the object 8. The foreign substance 81 has reflectance $n_{var81}$ which is smaller than the reflectance $n_{ob}$ of the object 8 ($n_{ob}>n_{var81}$). The foreign substance 82 has the reflectance $n_{var81}$ which is greater than the reflectance $n_{ob}$ of the object 8 ($n_{ob}<n_{var82}$).

Steps S1301 and S1302 are the same as Steps S701 and S702 described with reference to FIG. 7, and descriptions thereof are therefore omitted.

Step S1303: The light detection portion 7 (FIG. 10) receives a light beam reflected by the surface of the object 8 and transmitted through the converging section 5 and the beam splitter 6 (FIG. 10). The light detection portion 7 generates an electric current signal (light detection signal) I, which indicates the quantity of the received light. The electric current signal I generated by the light detection portion 7 is converted by the I-V converter 10 to an analog voltage signal xi (section (a) of FIG. 14). The analog voltage signal xi is converted by the AD converter 1011 to a digital voltage signal xi (section (b) of FIG. 14). In sections (a) and (b) of FIG. 14, the horizontal axis represents a scanning distance, and the vertical axis represents voltage.

Since the reflectance of the foreign substance 81 is smaller than the reflectance $n_{ob}$ of the object 8, the quantity of light reflected by the surface of the foreign substance 81 is relatively small (the quantity of light reflected from the object 8 sharply decreases when the light spot 16 reaches the foreign substance 81). Thus, as shown in section (a) of FIG. 14, the voltage signal, which corresponds to the light quantity, decreases when the light spot 16 passes over the foreign substance 81. On the other hand, since the reflectance of the foreign substance 82 is larger than the reflectance $n_{ob}$ of the object 8, the quantity of light reflected by the surface of the foreign substance 82 is relatively large (the quantity of light reflected from the object 8 sharply increases when the light spot 16 reaches the foreign substance 82). Thus, as shown in section (b) of FIG. 14, the voltage signal, which corresponds to the light quantity, increases when the light spot 16 passes over the foreign substance 82.

Step S1304: In the average value calculation section 1012, the voltage signal xi which indicates the quantity of light detected by the light detection section 7 is averaged for the entire surface, or a portion of the surface, of the object 8 onto which no foreign substance is attached, is averaged so as to obtain average voltage $X_{av}$, as described with reference to FIGS. 11(a) and 11(b).

Step S1305: In the reference value calculation section 1013, a first reference voltage $X_1$ and a second reference voltage $X_2$ are obtained using a function where the average voltage $X_{av}$ obtained at step S1304 is a variable. The first reference voltage $X_1$ and the second reference voltage $X_2$ are obtained according to the above described method.

Steps S1304 and S1305 may be performed before the start of a foreign substance detection operation, or may be performed for each a foreign substance detection operation.

Step S1306: The voltage signal xi obtained at step S1303 is compared with the first reference voltage $X_1$ and the second reference voltage $X_2$ calculated at step S1305. As described above with reference to FIG. 12, the first comparator 1014A compares the voltage signal xi with the first reference voltage $X_1$. The first comparator 1014A outputs a digital waveform signal (first comparison signal) $D_1$ wherein only a portion corresponding to the foreign substance 82 (region B in FIG. 14) is "1". The thus-obtained first digital signal waveform $D_1$ is shown in section (c) of FIG. 14. The second comparator 1014B compares the voltage signal xi with the second reference voltage $X_2$. The second comparator 1014B outputs a digital waveform signal (second comparison signal) $D_2$ wherein only a portion corresponding to the foreign substance 81 (region A in FIG. 14) is "1". The thus-obtained second digital signal waveform $D_2$ is shown in section (d) of FIG. 14.

Step S1307: The first digital waveform signal $D_1$ and second digital waveform signal $D_2$ generated at step S1306 are used to determine existence ranges of the foreign substances 81 and 82. As described above with reference to FIG. 12, a digital waveform signal $D_3$, where a portion corresponding to the foreign substance 81 (region A in FIG. 14) and a portion corresponding to the foreign substance 82 (region B in FIG. 14) are "1", is generated (see FIG. 14(e)). In sections (c) to (e) of FIG. 14, the horizontal axis represents a scanned distance, and the vertical axis represents a binary value (i.e., "0" or "1").

As described above, according to embodiment 2, a light detection signal and a reference value are used to determine an existence range of a foreign substance. A reference voltage is set using a function where an average value of an electric signal, which indicates the amount of light reflected from the surface of the object according to the environment in which a foreign substance existence determination apparatus is used, is used as a variable. Thus, a large margin of the reference voltage is secured for a variation in the quantity of light detected by the light detection section. Therefore, the foreign substance can be accurately detected. Furthermore, there are provided a reference value for detecting a foreign substance which has a reflectance smaller than that of the object and a reference value for detecting a foreign substance which has a reflectance greater than that of the object. Thus, the type of a foreign substance can also be determined.

In the case where the reflectance of an object and that of a foreign substance present thereon are substantially the same, the method of embodiment 2 is combined with the method of embodiment 1 so that the foreign substance can be readily detected.

A foreign substance existence range detection apparatus according to the present invention includes: a difference signal generation section for generating a difference signal which indicates a difference between a first light detection signal and a second light detection signal generated by the light detection section; a perimeter signal generation section for comparing the difference signal with a reference value to generate a perimeter signal which indicates a perimeter of a foreign substance; and a foreign substance determination section for determining an existence range of the foreign substance using the perimeter signal. In order to determine the existence range of the foreign substance, a signal in which noise is cancelled, and which has a higher signal quality than a conventionally-used sum signal, is used. Thus, the foreign substance existence range detection apparatus of the present invention can detect a foreign substance where a difference between the reflectance of an object and that of a foreign substance is small.

A foreign substance existence range detection apparatus according to the present invention includes: an average value calculation section for calculating an average value of a light detection signal which indicates the quantity of light reflected by a surface of an object; and a reference value calculation section for calculating a reference value from a function where the average value is a variable. With such a structure, the reference value can be set according to the environment in which the object is used. The foreign substance existence range detection apparatus of the present invention further includes: a comparison signal generation section for comparing the light detection signal with the reference value to generate a comparison signal which indicates presence/absence of a foreign substance; and a foreign substance determination section for determining an existence range of a foreign substance using the comparison signal. Since the reference value, which is determined according to the environment in which the object is used, and the light detection signal are compared to determine the existence range of the foreign substance, the existence range of the foreign substance can be determined with high accuracy even when a difference between the reflectance of the object and the reflectance of the foreign substance is small.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An apparatus for determining an existence range of a foreign substance which is present on a surface of an object, comprising:

an optical system including a light source for emitting a light beam onto the surface of the object;

a movement section for relatively moving the object with respect to the light beam;

a light detection section for detecting a light quantity of the light beam reflected by the surface of the object to generate a light detection signal which indicates the light quantity, the light detection section including a first light detection section for generating a first light detection signal and a second light detection section for generating a second light detection signal;

a difference signal generation section for generating a difference signal which indicates a difference between the first light detection signal and the second light detection signal;

a perimeter signal generation section for comparing the difference signal with a reference value to generate a perimeter signal which indicates a perimeter of the foreign substance, the reference value being an average of the actual light quantity measured under actual conditions in which the apparatus is used; and a foreign substance determination section for determining an existence range of the foreign substance using the perimeter signal.

2. An apparatus according to claim 1, wherein the first light detection section and the second light detection section are arranged along the moving direction in this order.

3. An apparatus according to claim 1, wherein the reference value varies according to an average value of the light quantity of the light beam reflected by the surface of the object on which the foreign substance is not attached.

4. An apparatus according to claim 1, wherein:

the optical system further includes a converging section for converging the light beam on the surface of the object; and the converging section is arranged such that the converged light beam has a wavefront aberration.

5. An apparatus according to claim 4, wherein:

the light beam is monochromic light; and a standard deviation of the wavefront aberration is 0.07 or more times a wavelength of the monochromic light.

6. An apparatus according to claim 4, further comprising a vibration section for vibrating the converging section along a direction parallel to the surface of the object.

7. An apparatus according to claim 1, wherein the movement section reciprocates the light beam along a direction parallel to the surface of the object.

8. An apparatus according to claim 7, further comprising a rotation section for rotating the object.

9. An apparatus according to claim 8, wherein the movement section oscillates the light beam in a direction perpendicular to the rotation direction of the object.

10. An apparatus according to claim 1, wherein the movement section reciprocates the object along a direction perpendicular to the emission direction of the light beam.

11. A method for determining an existence range of a foreign substance which is present on a surface of an object, comprising steps of:
 emitting a light beam onto the surface of the object;
 moving the object with respect to the light beam;
 detecting a light quantity of the light beam reflected by the surface of the object using a light detection section, to generate a light detection signal which indicates the light quantity, the light detection section including a first light detection section for generating a first light detection signal and a second light detection section for generating a second light detection signal;
 generating a difference signal which indicates a difference between the first light detection signal and the second light detection signal;
 comparing the difference signal with a reference value to generate a perimeter signal which indicates a perimeter of the foreign substance, the reference value being an average of the actual light quantity measured under actual conditions in which the apparatus is used; and
 determining an existence range of the foreign substance using the perimeter signal.

12. A method according to claim 11, wherein the first light detection section and the second light detection section are arranged along the moving direction in this order.

13. A method according to claim 11, wherein the reference value varies according to an average value of the light quantity of the light beam reflected by the surface of the object on which the foreign substance is not attached.

14. A method according to claim 11, further comprising a step of converging the light beam on the surface of the object, wherein the light beam converged on the surface of the object has a wavefront aberration.

15. A method according to claim 14, wherein:
 the light beam is monochromic light; and
 a standard deviation of the wavefront aberration is 0.07 or more times a wavelength of the monochromic light.

16. A method according to claim 14, wherein the step of converging the light beam includes a step of vibrating the light beam over the surface of the object.

17. A method according to claim 11, wherein the moving step includes a step of reciprocating the light beam along a direction parallel to the surface of the object.

18. A method according to claim 17, wherein the moving step includes a step of rotating the object.

19. A method according to claim 18, wherein the moving step includes a step of oscillating the light beam in a direction perpendicular to the rotation direction of the object.

20. A method according to claim 11, wherein the moving step includes a step of reciprocating the object along a direction perpendicular to the emission direction of the light beam.

21. An apparatus for determining an existence range of a foreign substance which is present on a surface of an object, comprising:
 an optical system including a light source for emitting a light beam onto the surface of the object;
 a movement section for relatively moving the object with respect to the light beam;
 a light detection section for detecting a light quantity of the light beam reflected by the surface of the object to generate a light detection signal which indicates the light quantity;
 an average value calculation section for calculating an average value of the light detection signal;
 a reference value calculation section for calculating a reference value using a function where the average value is a variable, the reference value being an average of the actual light quantity measured under actual conditions in which the apparatus is used;
 a comparison signal generation section for comparing the light detection signal with the reference value to generate a comparison signal which indicates presence/absence of the foreign substance; and
 a foreign substance determination section for determining an existence range of the foreign substance using the comparison signal.

22. An apparatus according to claim 21, wherein the average value is calculated by the average value calculation section by:
 obtaining an average value by averaging all values of the light detection signal which indicates the light quantity of the light beam reflected from the surface of the object on which the foreign substance is not attached; and
 averaging the values of the light detection signal which do not exceed a standard deviation of the obtained average value.

23. An apparatus according to claim 21, wherein:
 the reference value includes a first reference value $X_1$ and a second reference value $X_2$;
 the first reference value $X_1$ is used for detecting a foreign substance whose reflectance $n_{var}$ is larger than a reflectance $n_{ob}$ of the object ($n_{ob} < n_{var}$); and
 the second reference value $X_2$ is used for detecting a foreign substance whose reflectance $n_{var}$ is smaller than the reflectance $n_{ob}$ of the object ($n_{ob} > n_{var}$).

24. An apparatus according to claim 23, wherein the first reference value $X_1$ and the second reference value $X_2$ are calculated based on an arithmetic operation formula selected from a group consisting of following arithmetic operation formulas:

$$X_1 = X_{av} \cdot (1+\beta_1),\ X_2 = X_{av} \cdot (1-\alpha_1);$$

$$X_1 = X_{av}/(1-\alpha_2),\ X_2 = X_{av}/(1-\beta_2);\ \text{and}$$

$$X_1 = X_{av} + \beta_3,\ X_2 = X_{av} - \alpha_3,$$

where $X_{av}$ denotes the average value; $\alpha_1, \alpha_2, \alpha_3, \beta_1, \beta_2, \beta_3 > 0$; and $\alpha_1, \alpha_2, \alpha_3, \beta_1, \beta_2, \beta_3$ are constants.

25. An apparatus according to claim 21, wherein the movement section reciprocates the light beam along a direction parallel to the surface of the object.

26. An apparatus according to claim 25, further comprising a rotation section for rotating the object.

27. An apparatus according to claim 26, wherein the movement section oscillates the light beam in a direction perpendicular to the rotation direction of the object.

28. An apparatus according to claim 21, wherein the movement section reciprocates the object along a direction perpendicular to the emission direction of the light beam.

29. A method for determining an existence range of a foreign substance which is present on a surface of an object, comprising steps of:

emitting a light beam onto the surface of the object;

moving the object with respect to the light beam;

detecting a light quantity of the light beam reflected by the surface of the object to generate a light detection signal which indicates the light quantity;

calculating an average value of the light detection signal;

calculating a reference value using a function where the average value is a variable, the reference value being an average of the actual light quantity measured under actual conditions in which the apparatus is used;

comparing the light detection signal with the reference value to generate a comparison signal which indicates presence/absence of the foreign substance; and determining an existence range of the foreign substance using the comparison signal.

30. A method according to claim 29, wherein the step of calculating the average value includes:

obtaining an average value by averaging all values of the light detection signal which indicates the light quantity of the light beam reflected from the surface of the object on which the foreign substance is not attached; and averaging the values of the light detection signal which do not exceed a standard deviation of the obtained average value.

31. A method according to claim 29, wherein:

the reference value includes a first reference value $X_1$ and a second reference value $X_2$;

the first reference value $X_1$ is used for detecting a foreign substance whose reflectance $n_{var}$ is larger than a reflectance $n_{ob}$ of the object ($n_{ob} < n_{var}$); and the second reference value $X_2$ is used for detecting a foreign substance whose reflectance $n_{var}$ is smaller than the reflectance $n_{ob}$ of the object ($n_{ob} > n_{var}$).

32. A method according to claim 31, wherein the step of calculating the reference value includes a step of obtaining the first reference value $X_1$ and the second reference value $X_2$ based on an arithmetic operation formula selected from a group consisting of following arithmetic operation formulas:

$$X_1 = X_{av} \cdot (1+\beta_1),\ X_2 = X_{av} \cdot (1-\alpha_1);$$

$$X_1 = X_{av}/(1-\alpha_2),\ X_2 = X_{av}/(1=\beta_2);\ \text{and}$$

$$X_1 = X_{av} + \beta_3,\ X_2 = X_{av} - \alpha_3,$$

where $X_{av}$ denotes the average value; $\alpha_1$, $\alpha_2$, $\alpha_3$, $\beta_1$, $\beta_2$, $\beta_3 > 0$; and $\alpha_1$, $\alpha_2$, $\alpha_3$, $\beta_1$, $\beta_2$, $\beta_3$ are constants.

33. A method according to claim 29, wherein the moving step includes a step of reciprocating the light beam along a direction parallel to the surface of the object.

34. A method according to claim 33, wherein the moving step includes a step of rotating the object.

35. A method according to claim 34, wherein the moving step includes a step of oscillating the light beam in a direction perpendicular to the rotation direction of the object.

36. A method according to claim 29, wherein the moving step includes a step of reciprocating the object along a direction perpendicular to the emission direction of the light beam.

* * * * *

UNITED STATES PATENT AND TRADEMARK OFFICE
CERTIFICATE OF CORRECTION

PATENT NO. : 6,791,681 B2  
APPLICATION NO. : 10/172084  
DATED : September 14, 2004  
INVENTOR(S) : Gotoh et al.

It is certified that error appears in the above-identified patent and that said Letters Patent is hereby corrected as shown below:

On the title page item (75), should read:  
--Yasuhiro GOTOH resides in Osaka, Japan and Seiji NISHIWAKI resides in Hyogo, Japan--.

Col. 22, In claim 24, the equation should read as follows:

$X_1 = X_{av}/(1-\alpha_2)$, $X_2 = X_{av}/(1+\beta_2)$; and....

Col. 24, In claim 32, line 6, the equation should read as follows:

$X_1 = X_{av}/(1-\alpha_2)$, $X_2 = X_{av}/(1+\beta_2)$; and....

Signed and Sealed this

Twenty-sixth Day of June, 2007

JON W. DUDAS  
*Director of the United States Patent and Trademark Office*